United States Patent
McCook et al.

(10) Patent No.: US 10,588,859 B2
(45) Date of Patent: *Mar. 17, 2020

(54) TOPICAL FORMULATIONS HAVING ENHANCED BIOAVAILABILITY

(71) Applicant: Berg LLC, Framingham, MA (US)

(72) Inventors: John Patrick McCook, Frisco, TX (US); Indushekhar Persaud, Homestead, FL (US); Niven Rajin Narain, Cambridge, MA (US)

(73) Assignee: Berg LLC, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/751,769

(22) Filed: Jan. 28, 2013

(65) Prior Publication Data

US 2013/0202683 A1 Aug. 8, 2013

Related U.S. Application Data

(63) Continuation of application No. 12/052,825, filed on Mar. 21, 2008, now Pat. No. 8,454,945.

(60) Provisional application No. 60/919,554, filed on Mar. 22, 2007.

(51) Int. Cl.

| | | |
|---|---|---|
| *A61K 31/00* | (2006.01) | |
| *A61K 31/122* | (2006.01) | |
| *A61K 9/127* | (2006.01) | |
| *A61K 47/10* | (2017.01) | |
| *A61K 47/14* | (2017.01) | |
| *A61K 47/34* | (2017.01) | |
| *A61K 8/35* | (2006.01) | |
| *A61K 47/02* | (2006.01) | |
| *A61K 47/24* | (2006.01) | |
| *A61K 8/14* | (2006.01) | |
| *A61K 47/26* | (2006.01) | |
| *A61K 9/00* | (2006.01) | |
| *A61K 47/18* | (2017.01) | |
| *A61K 47/12* | (2006.01) | |
| *A61Q 19/00* | (2006.01) | |

(52) U.S. Cl.
CPC ............... *A61K 9/127* (2013.01); *A61K 8/14* (2013.01); *A61K 8/355* (2013.01); *A61K 9/0014* (2013.01); *A61K 31/122* (2013.01); *A61K 47/02* (2013.01); *A61K 47/10* (2013.01); *A61K 47/12* (2013.01); *A61K 47/14* (2013.01); *A61K 47/186* (2013.01); *A61K 47/24* (2013.01); *A61K 47/26* (2013.01); *A61K 47/34* (2013.01); *A61Q 19/00* (2013.01)

(58) Field of Classification Search
None
See application file for complete search history.

(56) References Cited

U.S. PATENT DOCUMENTS

| | | |
|---|---|---|
| 4,515,736 A | 5/1985 | Deamer |
| 4,525,350 A | 6/1985 | Casey et al. |
| 4,636,381 A | 1/1987 | Takada et al. |
| 4,654,373 A | 3/1987 | Bertelli |
| 4,895,727 A | 1/1990 | Allen |
| 5,015,483 A | 5/1991 | Haynes et al. |
| 5,362,494 A | 11/1994 | Zysman et al. |
| 5,378,461 A | 1/1995 | Neigut |
| 5,602,184 A | 2/1997 | Myers et al. |
| 5,603,958 A | 2/1997 | Morein et al. |
| 5,651,991 A | 7/1997 | Sugiyama et al. |
| 5,700,482 A | 12/1997 | Frederiksen et al. |
| 5,770,222 A | 6/1998 | Unger et al. |
| 5,876,737 A | 3/1999 | Schönrock et al. |
| 5,889,062 A | 3/1999 | Hoppe et al. |
| 5,891,465 A | 4/1999 | Keller et al. |
| 5,912,272 A | 6/1999 | Hoppe et al. |
| 5,944,012 A | 8/1999 | Pera |
| 5,962,243 A | 10/1999 | Brown et al. |
| 6,005,086 A | 12/1999 | Evans et al. |
| 6,048,886 A | 4/2000 | Neigut |
| 6,071,495 A | 6/2000 | Unger et al. |
| 6,184,353 B1 | 2/2001 | Evans et al. |
| 6,228,891 B1 | 5/2001 | Enzmann et al. |
| 6,261,575 B1 | 7/2001 | Hoppe et al. |
| 6,372,234 B1 | 4/2002 | Deckers et al. |
| 6,416,957 B1 | 7/2002 | Evans et al. |
| 6,461,593 B1 | 10/2002 | Hanioka et al. |
| 6,468,552 B1 | 10/2002 | Stahl et al. |
| 6,482,943 B1 | 11/2002 | Bolkhin et al. |
| 6,503,523 B2 | 1/2003 | Hoppe et al. |
| 6,506,915 B1 | 1/2003 | West |
| 6,511,800 B1 | 1/2003 | Singh |
| 6,531,117 B2 | 3/2003 | Heger et al. |
| 6,573,284 B1 | 6/2003 | Riley et al. |

(Continued)

FOREIGN PATENT DOCUMENTS

| | | |
|---|---|---|
| EP | 1849481 A1 | 10/2007 |
| WO | WO 93/16704 A1 | 9/1993 |

(Continued)

OTHER PUBLICATIONS

Gura, Science, 1997, 278: 1-4.*

(Continued)

*Primary Examiner* — Ileana Popa

(74) *Attorney, Agent, or Firm* — McCarter & English, LLP; Jill Mello

(57) ABSTRACT

The present disclosure provides compositions suitable for delivering lipophilic bioactive agents. The compositions may be utilized to treat numerous diseases and conditions that would benefit from the application of a lipophilic bioactive agent.

28 Claims, 1 Drawing Sheet

(56) References Cited

U.S. PATENT DOCUMENTS

| | | |
|---|---|---|
| 6,576,660 B1 | 6/2003 | Liao et al. |
| 6,576,678 B1 | 6/2003 | Bruening et al. |
| 6,582,710 B2 | 6/2003 | Deckers et al. |
| 6,582,723 B2 | 6/2003 | Gorsek |
| 6,596,287 B2 | 6/2003 | Deckers et al. |
| 6,599,513 B2 | 7/2003 | Deckers et al. |
| 6,623,746 B1 | 9/2003 | Wadle et al. |
| 6,630,160 B1 | 10/2003 | Evans et al. |
| 6,652,891 B2 | 11/2003 | Selzer |
| 6,686,485 B2 | 2/2004 | West |
| 6,696,484 B2 | 2/2004 | Liao et al. |
| 6,727,234 B2 | 4/2004 | Wiemer et al. |
| 6,733,790 B1 | 5/2004 | Garces Garces |
| 6,753,325 B2 | 6/2004 | Rosenbloom |
| 6,803,193 B1 | 10/2004 | Hopper et al. |
| 6,806,069 B2 | 10/2004 | Chokshi |
| 6,809,176 B2 | 10/2004 | Blokhin et al. |
| 6,867,024 B2 | 3/2005 | Chokshi |
| 6,906,106 B2 | 6/2005 | Chevalier |
| 7,083,572 B2 | 8/2006 | Unger et al. |
| 7,083,780 B2 | 8/2006 | Ansmann et al. |
| 7,091,241 B2 | 8/2006 | Gilloteaux et al. |
| 7,101,536 B2 | 9/2006 | Mongiat et al. |
| 7,132,268 B2 | 11/2006 | Miyake et al. |
| 7,147,841 B2 | 12/2006 | Herzog |
| 7,169,385 B2 | 1/2007 | Fantuzzi et al. |
| 7,169,590 B2 | 1/2007 | Ueda et al. |
| 7,176,171 B2 | 2/2007 | Nieendick et al. |
| 7,179,880 B2 | 2/2007 | Kawa et al. |
| 7,182,938 B2 | 2/2007 | Andre et al. |
| 7,198,801 B2 | 4/2007 | Carrara et al. |
| 7,208,298 B2 | 4/2007 | Miyake et al. |
| 7,250,174 B2 | 7/2007 | Lee et al. |
| 7,268,107 B2 | 9/2007 | Nieendick et al. |
| 7,273,606 B2 | 9/2007 | Fantuzzi et al. |
| 7,279,456 B2 | 10/2007 | Dufay |
| 7,311,897 B2 | 12/2007 | Ehlis et al. |
| 7,318,929 B2 | 1/2008 | Schieferstein et al. |
| 7,357,918 B2 | 4/2008 | Comte et al. |
| 2001/0022965 A1 | 9/2001 | Heger et al. |
| 2002/0039595 A1 | 4/2002 | Keller |
| 2002/0044913 A1 | 4/2002 | Hamilton |
| 2002/0048559 A1 | 4/2002 | Shinoda et al. |
| 2002/0049422 A1 | 4/2002 | Brewitt |
| 2002/0071852 A1 | 6/2002 | Deckers et al. |
| 2002/0106337 A1 | 8/2002 | Deckers et al. |
| 2002/0114820 A1 | 8/2002 | Deckers et al. |
| 2002/0127252 A1 | 9/2002 | Kramer et al. |
| 2002/0155151 A1 | 10/2002 | Enzmann et al. |
| 2002/0156302 A1 | 10/2002 | West |
| 2002/0182199 A1 | 12/2002 | Hoppe et al. |
| 2003/0012762 A1 | 1/2003 | Zulli et al. |
| 2003/0031688 A1 | 2/2003 | Ghosh et al. |
| 2003/0044441 A1 | 3/2003 | Schmid et al. |
| 2003/0077297 A1 | 4/2003 | Chen et al. |
| 2003/0091518 A1 | 5/2003 | Pauly et al. |
| 2003/0104048 A1 | 6/2003 | Patel et al. |
| 2003/0104080 A1 | 6/2003 | Singh et al. |
| 2003/0105030 A1 | 6/2003 | Liao et al. |
| 2003/0105031 A1 | 6/2003 | Rosenbloom |
| 2003/0108493 A1 | 6/2003 | Henry et al. |
| 2003/0113354 A1 | 6/2003 | Schmid et al. |
| 2003/0118576 A1 | 6/2003 | Brancato et al. |
| 2003/0124158 A1 | 7/2003 | Heidenfelder et al. |
| 2003/0129150 A1 | 7/2003 | Pauly et al. |
| 2003/0143166 A1 | 7/2003 | Heger et al. |
| 2003/0144346 A1 | 7/2003 | Liao et al. |
| 2003/0152598 A1 | 8/2003 | Heidenfelder et al. |
| 2003/0161849 A1 | 8/2003 | Heidenfelder et al. |
| 2003/0167556 A1 | 9/2003 | Kelley |
| 2003/0170265 A1 | 9/2003 | Henry et al. |
| 2003/0180231 A1 | 9/2003 | Danoux et al. |
| 2003/0180278 A1 | 9/2003 | Hoppe et al. |
| 2003/0180352 A1 | 9/2003 | Patel et al. |
| 2003/0185865 A1 | 10/2003 | Jentzsch et al. |
| 2003/0215406 A1 | 11/2003 | Schreiner et al. |
| 2003/0219472 A1 | 11/2003 | Pauletti et al. |
| 2004/0028614 A1 | 2/2004 | Corbella et al. |
| 2004/0034107 A1 | 2/2004 | Enzmann |
| 2004/0043045 A1 | 3/2004 | Seipel et al. |
| 2004/0063648 A1 | 4/2004 | Pandol et al. |
| 2004/0067260 A1 | 4/2004 | Milley et al. |
| 2004/0086538 A1 | 5/2004 | Sauermann et al. |
| 2004/0109880 A1 | 6/2004 | Pauly et al. |
| 2004/0110848 A1 | 6/2004 | Peffley et al. |
| 2004/0122109 A1 | 6/2004 | Fujii et al. |
| 2004/0126367 A1 | 7/2004 | Fujii et al. |
| 2004/0142006 A1 | 7/2004 | Bleckmann et al. |
| 2004/0142007 A1 | 7/2004 | Moussou et al. |
| 2004/0142009 A1 | 7/2004 | Ansmann et al. |
| 2004/0151710 A1 | 8/2004 | Bozzacco |
| 2004/0170581 A1 | 9/2004 | Henry et al. |
| 2004/0185071 A1 | 9/2004 | Hatazaki |
| 2004/0191190 A1 | 9/2004 | Pauly et al. |
| 2004/0191263 A1 | 9/2004 | Hageman et al. |
| 2004/0197279 A1 | 10/2004 | Bleckmann et al. |
| 2004/0197354 A1 | 10/2004 | Doring et al. |
| 2004/0219114 A1 | 11/2004 | Andersson et al. |
| 2004/0228910 A1 | 11/2004 | Enzmann et al. |
| 2004/0234559 A1 | 11/2004 | Bleckmann et al. |
| 2004/0258717 A1 | 12/2004 | Sauermann et al. |
| 2005/0000390 A1 | 1/2005 | Nieendick et al. |
| 2005/0000726 A1 | 1/2005 | Kimata et al. |
| 2005/0008581 A1 | 1/2005 | Parkhideh |
| 2005/0019278 A1 | 1/2005 | Berg-Schultz |
| 2005/0019353 A1 | 1/2005 | Prinz et al. |
| 2005/0036976 A1 | 2/2005 | Rubin et al. |
| 2005/0037036 A1 | 2/2005 | Nielsen et al. |
| 2005/0058610 A1 | 3/2005 | Baschong et al. |
| 2005/0069582 A1 | 3/2005 | Fantuzzi |
| 2005/0070611 A1 | 3/2005 | Fantuzzi |
| 2005/0079164 A1 | 4/2005 | Fantuzzi et al. |
| 2005/0100537 A1 | 5/2005 | Evans et al. |
| 2005/0106190 A1 | 5/2005 | Kawa et al. |
| 2005/0106199 A1 | 5/2005 | Schreiber et al. |
| 2005/0112156 A1 | 5/2005 | Busch et al. |
| 2005/0118209 A1 | 6/2005 | Jentszch et al. |
| 2005/0136081 A1 | 6/2005 | Kawa et al. |
| 2005/0142123 A1 | 6/2005 | Chen et al. |
| 2005/0142153 A1 | 6/2005 | Schreiber et al. |
| 2005/0147598 A1 | 7/2005 | Ueda et al. |
| 2005/0152856 A2 | 7/2005 | Andersson et al. |
| 2005/0214333 A1 | 9/2005 | Lanzendoerfer et al. |
| 2005/0220826 A1 | 10/2005 | Kawa et al. |
| 2005/0226824 A1 | 10/2005 | Kawa et al. |
| 2005/0226858 A1 | 10/2005 | Kitamura et al. |
| 2005/0226947 A1 | 10/2005 | Kern |
| 2005/0238679 A1 | 10/2005 | Biergiesser et al. |
| 2005/0255057 A1 | 11/2005 | Andre et al. |
| 2005/0276764 A1 | 12/2005 | Kolbe et al. |
| 2005/0281772 A1 | 12/2005 | Bromley et al. |
| 2005/0287206 A1 | 12/2005 | Fantuzzi et al. |
| 2006/0002964 A9 | 1/2006 | Schreiber et al. |
| 2006/0008482 A1 | 1/2006 | Prinz et al. |
| 2006/0010519 A1 | 1/2006 | Kadowaki et al. |
| 2006/0013888 A1 | 1/2006 | Fantuzzi |
| 2006/0035981 A1 | 2/2006 | Mazzio et al. |
| 2006/0039956 A1 | 2/2006 | Hensen et al. |
| 2006/0051462 A1 | 3/2006 | Wang |
| 2006/0073106 A1 | 4/2006 | Berg-Schultz et al. |
| 2006/0093633 A1 | 5/2006 | Stab et al. |
| 2006/0099158 A1 | 5/2006 | Zander et al. |
| 2006/0121016 A1 | 6/2006 | Lee |
| 2006/0127384 A1 | 6/2006 | Capaccioli et al. |
| 2006/0153783 A1 | 7/2006 | Ehlis et al. |
| 2006/0188459 A1 | 8/2006 | Heinrichs et al. |
| 2006/0188492 A1 | 8/2006 | Richardson et al. |
| 2006/0193905 A1 | 8/2006 | Ehringer et al. |
| 2006/0204458 A1* | 9/2006 | Holloway, Jr. .......... A61K 8/02 424/59 |
| 2006/0251690 A1 | 11/2006 | Lipshutz et al. |
| 2006/0251708 A1 | 11/2006 | Chen et al. |
| 2006/0286046 A1 | 12/2006 | Haber |
| 2006/0292220 A1 | 12/2006 | Giordano et al. |

(56) References Cited

U.S. PATENT DOCUMENTS

| | | |
|---|---|---|
| 2007/0053985 A1 | 3/2007 | Ueda et al. |
| 2007/0071779 A1 | 3/2007 | McKie |
| 2007/0085059 A1 | 4/2007 | Mora-Gutierrez et al. |
| 2007/0092469 A1 | 4/2007 | Jacobs |
| 2007/0104701 A1 | 5/2007 | Ueda et al. |
| 2007/0104810 A1 | 5/2007 | Kern |
| 2007/0110731 A1 | 5/2007 | Riley |
| 2007/0172436 A1 | 7/2007 | Zhang |
| 2007/0184041 A1 | 8/2007 | Burja |
| 2007/0184076 A1 | 8/2007 | Unger et al. |
| 2007/0189994 A1 | 8/2007 | Berg et al. |
| 2007/0196349 A1 | 8/2007 | Kitamura et al. |
| 2007/0196914 A1 | 8/2007 | Murray et al. |
| 2007/0202090 A1 | 8/2007 | Prosek et al. |
| 2007/0218042 A1 | 9/2007 | Khaled |
| 2007/0243180 A1 | 10/2007 | Tanaka et al. |
| 2007/0248590 A1 | 10/2007 | Milne et al. |
| 2007/0253941 A1 | 11/2007 | Naidu et al. |
| 2007/0258966 A1 | 11/2007 | Ueda et al. |
| 2007/0258967 A1 | 11/2007 | Ueda et al. |
| 2007/0275021 A1 | 11/2007 | Lee et al. |
| 2008/0020022 A1 | 1/2008 | Udell |
| 2008/0025929 A1 | 1/2008 | Burton et al. |
| 2008/0031862 A1 | 2/2008 | Ghosal |
| 2008/0063674 A1 | 3/2008 | Vollhardt et al. |
| 2008/0069779 A1 | 3/2008 | Tamarkin et al. |
| 2008/0069898 A1 | 3/2008 | Smith et al. |
| 2008/0075684 A1 | 3/2008 | Barg et al. |
| 2008/0081034 A1 | 4/2008 | Zimmerman et al. |
| 2008/0081082 A1 | 4/2008 | Zimmerman et al. |
| 2008/0089852 A1 | 4/2008 | Hotz et al. |
| 2008/0089913 A1 | 4/2008 | Kallmayer et al. |
| 2008/0095719 A1 | 4/2008 | Herrmann et al. |
| 2008/0102313 A1 | 5/2008 | Nilsen et al. |
| 2008/0207560 A1* | 8/2008 | Harada ............... A61K 8/34 514/54 |
| 2011/0110914 A1* | 5/2011 | Narain et al. ............. 424/94.5 |

FOREIGN PATENT DOCUMENTS

| | | |
|---|---|---|
| WO | WO 96/17626 A2 | 6/1996 |
| WO | WO 02/078727 A1 | 10/2002 |
| WO | WO 04/003564 A2 | 1/2004 |
| WO | WO 05/069916 A2 | 8/2005 |
| WO | WO 2006/073190 A1 | 7/2006 |

OTHER PUBLICATIONS

Frijhof et al., Molecular Carcinogenesis, 2004, 39: 183-194.*
Lesperance et al., Breast Cancer Res. Treat., 2002, 76: 137-143, Abstract.*
Khavari, Nature Reviews, 2006, 6: 270-280.*
Bliznakov, E., et al., "Coenzymes Q: Stimulants of the Phagocytic Activity in Rats and Immune Response in Mice", *Experientia*, 26(9): 953-954 (Sep. 1970).
Bliznakov, E., "Effect of Stimulation of the Host Defense System" by Coenzyme Q10 on Dibenzpyrene-Induces Tumors and Infection with Friend Leukemia Virus in Mice, *Proc. Nat. Acad. Sci. USA*, 70(2): 390-394 (Feb. 1973).
Hodges, et al., "CoQ10: could it have a role in cancer management?", *BioFactors*, vol. 9, pp. 365-370 (1999).
Kokawa, T., et al., "Coenzyme Q10 in cancer chemotherapy-experimental studies on augmentation of the effects of masked compounds, especially in the combined chemotherapy with immunopotentiators", XP-002473825 Database accession No. NLM6681995 (Mar. 1983) (Abstract only).
Lockwood, et al., "Progress on therapy of breast cancer with vitamin Q10 and the regression of metastases", *Biochem-Biophy-Res-Commun* 212(1) pp. 172-177 (1995) (Abstract only).
Lockwood, et al., "Apparent partial remission of breast cancer in 'high risk' patients supplemented with nutritional antioxidants, essential fatty acids and coenzyme Q10", *Mol-Aspects-Med.*, vol. 15, Suppl. pp. 231-240 (1994) (Abstract only).
Lockwood, et al., "Partial and complete regression of breast cancer in patients in relation to dosage of coenzyme Q10", *Biochem-Biophys-Res-Commun.*, 199(3), pp. 1504-1506 (1994) (Abstract only).
Mura, P., et al., "Evaluation of transcutol as a clonazepam transdermal permeation enhancer from hydrophilic gel formulations", *European Journal of Pharmaceutical Sciences*. 9 pgs. 365-372 (2000).
Supplementary European Search Report from Application No. EP 05 71 1599 dated Apr. 10, 2008.
International Search Report from Application No. PCT/US2007/068052 dated Apr. 15, 2008.
International Search Report from Application No. PCT/US2008/057786 dated Oct. 23, 2008.
U.S. Appl. No. 12/052,825/U.S. Pat. No. 8,454,945, filed Mar. 21, 2008/dated Jun. 4, 2013, US 2008-0233183 A1, Issued.
U.S. Appl. No. 13/046,221, filed Mar. 11, 2011, US 2011-0229554 A1, Pending.
U.S. Appl. No. 12/746,117, filed Feb. 28, 2011, US 2011-0142914 A1, Pending.
U.S. Appl. No. 13/526,333, filed Jun. 18, 2012, US 2012-0321698 A1, Pending.
U.S. Appl. No. 12/778,094, filed May 11, 2010, US 2011-0027247 A1, Abandoned.
U.S. Appl. No. 14/171,419, filed Feb. 3, 2014, US 2015-0023940 A1, Pending.
U.S. Appl. No. 12/777,902, filed May 11, 2010, US 2011-0110914 A1, Pending.

* cited by examiner

Figure 1: Mean ± SD CoQ$_{10}$ Epidermal Concentration vs Dose (Male Pig):
(n=6/skin section)
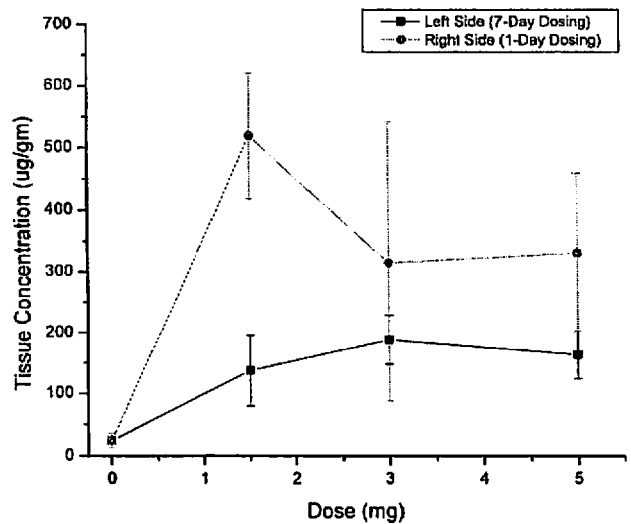
Figure 2: Mean ± SD CoQ$_{10}$ Epidermal Concentration vs Dose (Female Pig):
(n=6/skin section)
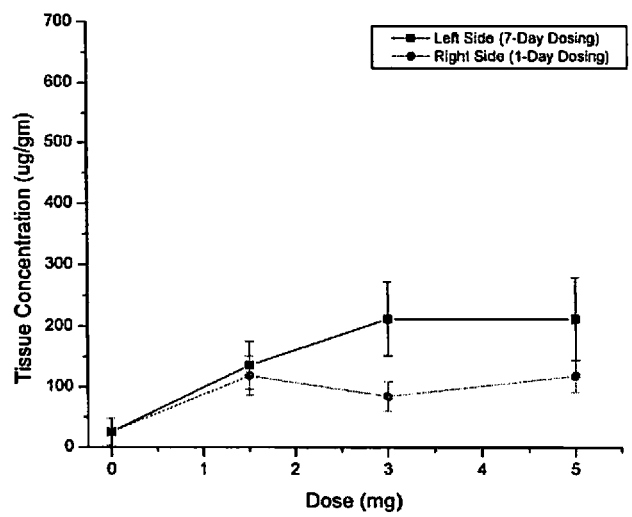

TOPICAL FORMULATIONS HAVING ENHANCED BIOAVAILABILITY

CROSS-REFERENCE TO RELATED APPLICATIONS

This application is a continuation of U.S. patent application Ser. No. 12/052,825, filed Mar. 21, 2008, which claims the benefit of and priority to U.S. Provisional Application Ser. No. 60/919,554, filed Mar. 22, 2007, the entire disclosure of which is incorporate by reference herein.

BACKGROUND

Cancer is presently one of the leading causes of death in developed nations. Although recent research has vastly increased our understanding of many of the molecular mechanisms of tumorigenesis and has provided numerous new avenues for the treatment of cancer, standard treatments for most malignancies remain gross resection, chemotherapy, and radiotherapy. While increasingly successful, each of these treatments may cause numerous undesired side effects. For example, surgery may result in pain, traumatic injury to healthy tissue, and scarring. Radiotherapy and chemotherapy may cause nausea, immune suppression, gastric ulceration and secondary tumorigenesis.

Improved methods for the treatment of diseases, including cancer, and compositions capable of delivering bioactive agents to aid in the treatment of diseases and other conditions remain desirable.

SUMMARY

The present disclosure provides compositions suitable for administering lipophilic bioactive agents to a subject. The lipophilic bioactive agents may be delivered by any route of administration. In embodiments, the lipophilic bioactive agent may be contained in liposomes.

Methods for forming compositions containing liposomes possessing lipophilic bioactive agents are also provided. In embodiments the lipophilic bioactive agent may be prepared as a first phase, optionally in combination with a solubilizer, while a second phase may be prepared containing at least one phospholipid. The two phases may be combined, thereby forming liposomes possessing lipophilic bioactive agent.

In embodiments, liposomes possessing lipophilic bioactive agent may be combined with additional carriers for administration to a subject. Such carriers may include, in embodiments, oil phases, water phases, neutralizing or buffer phases, pigments, combinations thereof, and the like.

Compositions of the present disclosure including liposomes possessing lipophilic bioactive agents may also include permeation enhancers to enhance delivery of the bioactive agent.

In embodiments, compositions of the present disclosure may include a liposomal concentrate including a phospholipid such as lecithin, lysolecithin, phosphatidylcholine, phosphatidylethanolamine, phosphatidylinositol, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, and combinations thereof, at least one lipophilic bioactive agent, and at least one solubilizer. The liposomal concentrate may be in combination with at least one pharmaceutically acceptable carrier possessing at least one permeation enhancer in an amount from about 0.5% by weight to about 20% by weight of the composition. The phospholipid may present in the composition in an amount from about 2% to about 20% by weight of the composition and the bioactive agent may be present in an amount from about 0.5% to about 20% by weight of the composition.

In other embodiments, a composition of the present disclosure may include an oil phase, a water phase, a neutralization phase, a pigment phase, and a liposomal concentrate. The oil phase may include C12-15 alkyl benzoates, cetyl alcohol, stearyl alcohol, glyceryl stearate, and polyethylene glycol 100 stearate, and may be present in an amount of from about 5% to about 20% by weight of the composition. The water phase may include glycerin, propylene glycol, ethoxydiglycol, phenoxyethanol, water, and a crosslinked acrylic acid polymer dispersion including phenoxyethanol, propylene glycol, water, and a crosslinked acrylic acid polymer, and may be present in an amount of from about 60 to about 80% by weight of the composition. The neutralization phase may include water, triethanolamine, sodium lactate, and lactic acid, and may be present in an amount of from about 0.1% to about 15% by weight of the composition. The pigment may include titanium dioxide present in an amount of from about 0.2% to about 2% by weight of the composition. The liposomal concentrate may include a polyethoxylated fatty acid ester of sorbitan, coenzyme Q10, a phosphatidylcholine lecithin, phenoxyethanol, propylene glycol, and water, and may be present in an amount of from about 0.1% to about 30% by weight of the composition. In embodiments, the propylene glycol and ethoxydiglycol from the water phase may act as permeation enhancers and may be present in a combined amount of from 3% by weight to about 15% by weight of the composition, and the coenzyme Q10 may be present in an amount of from about 0.75% by weight to about 10% by weight of the composition.

Any disease or condition that would benefit from the administration of a lipophilic bioactive agent may be treated with liposomes possessing lipophilic bioactive agents as described herein, including compositions containing such liposomes possessing lipophilic bioactive agents optionally in combination with a permeation enhancer.

BRIEF DESCRIPTION OF THE FIGURES

Various embodiments of the present disclosure will be described herein below with reference to the Figures wherein:

FIG. 1 is a graph depicting the epidermal CoQ10 concentration in a male pig after treatment with a composition of the present disclosure having a permeation enhancer; and FIG. 2 is a graph depicting the epidermal CoQ10 concentration in a female pig after treatment with a control composition.

DETAILED DESCRIPTION

In accordance with the present disclosure, a formulation is provided for improved administration of lipophilic bioactive agents, which may also be referred to herein as hydrophobic bioactive agents. As used herein, a lipophilic bioactive agent includes an agent that is insoluble in water. Specifically, lipophilic bioactive agents, as used herein, will have a solubility in water that is less than about 1 part of bioactive drug in about 1000 parts of water.

In embodiments the lipophilic bioactive agents may be placed in liposomes and administered to a patient. In accordance with the present disclosure, any phospholipid and/or phospholipid derivative such as a lysophospholipid may be utilized to form a liposome for encapsulating the lipophilic bioactive agent. Suitable phospholipids and/or phospholipid derivatives include, but are not limited to, lecithin, lysolecithin, phosphatidylcholine, phosphatidylethanolamine, phosphatidylinositol, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, combinations thereof, and the like.

In some embodiments, a lecithin derived from egg or soybean may be utilized as the phospholipid. Such lecithins include those commercially available as PHOSPHOLIPON® 85G, PHOSPHOLIPON® 90G, and PHOSPHOLIPON® 90H (the fully hydrogenated version of PHOSPHOLIPON® 90G) from American Lecithin Company, Oxford, Conn. Other suitable lecithins include LECINOL S-10® lecithin from Nikko Chemicals.

The above phospholipids or derivatives thereof may be utilized to form liposomes containing the bioactive agent. In embodiments, a lecithin having a high phosphatidylcholine content may be utilized to form a liposome. In some embodiments a high phosphatidylcholine lecithin which may be utilized includes PHOSPHOLIPON® 85G, a soy-derived lecithin containing a minimum of about 85% of a linoleic acid based-phosphatidylcholine. This lecithin is easy to use and is able to produce submicron liposomes at low process temperatures (from about 20° C. to about 55° C.) without the addition of any other special additives. PHOSPHOLIPON® 85G contains, in addition to phosphatidylcholine, approximately 5-7% phosphatidic acid. The phosphatidic acid confers a negative surface charge to the resulting liposome vesicles, reduces processing time and process energy, and aids in the formation of stable liposomes.

Suitable lipophilic bioactive agents which may be enclosed in liposomes herein include, but are not limited to, analgesics, anti-inflammatory agents, anthelmintics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-Blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leucotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, external analgesics (for example aspirin, nonsteroidal anti-inflammatories and the like), steroidal antiinflammatory drugs (such as hydrocortisone and the like), skin bleaching agents (such as hydroquinone, kojic acid, sodium metabisulfite, and the like), skin protectants, and combinations thereof.

Specific, non-limiting examples of suitable lipophilic bioactive agents include, but are not limited to, acutretin, albendazole, albuterol, aminogluthemide, amiodarone, amlodipine, amphetamine, amphotericin B, atorvastatin, atovaquone, azithromycin, baclofen, beclomethsone, benezepril, benzonatate, benzoquinones, betamethasone, bicalutanide, budesonide, bupropion, busulphan, butenafine, calcifediol, calciprotiene, calcitriol, camptothecan, candesartan, capsaicin, carbamezepine, carotenes, celecoxib, cerivistatin, cetrizine, chlorpheniramine, cholecalciferol, cilostazol, cimetidine, cinnarizine, ciprofloxacin, cisapride, clarithromycin, clemastine, clomiphene, clomipramine, clopidrogel, codeine, coenzyme Q10, cyclobenzaprine, cyclosporine, danazol, dantrolene, dexchlopheniramine, diclofenac, dicoumarol, digoxin, dihydro epiandrosterone, dihydroergotamine, dihydrotachysterol, dirithromycin, donepezil, efavirenz, eposartan, ergocalciferol, ergotamine, essential fatty acid sources, etodolac, etoposide, famotidine, farnesol, fenofibrate, fentanyl, fexofenadine, finasteride, flucanazole, flurbiprofen, fluvastatin, fosphenylion, frovatriptan, furazolidone, gabapentin, gemfibrozil, glibenclamide, glipizide, glyburide, glymepride, griseofulvin, halofantrine, ibuprofen, irbesartan, irinotecan, isoprenoids, isosorbide dinitrate, isotreinoin, itraconazole, ivermectin, ketoconazole, ketorolac, lamotrigine, lanosprazole, leflunomide, lisinopril, loperamide, loratadine, lovastatin, L-thryroxine, lutein, lycopene, medroxyprogesterone, mefepristone, mefloquine, megesterol acetate, methadone, methoxsalen, metronidazole, metronidazole, miconazole, midazolam, miglitol, minoxidil, mitoxantrone, montelukast, nabumetone, nalbuphine, naratiptan, nelfinavir, nifedipine, nilsolidipine, nilutanide, nitrofurantoin, nizatidine, omeprazole, oprevelkin, osteradiol, oxaprozin, paclitaxel, paricalcitol, paroxetine, pentazocine, pioglitazone, pizofetin, pravastatin, prednisolone, probucol, progesterone, pseudo-ephedrine, pyridostigmine, rabeprazole, raloxifene, refocoxib, repaglinide, rifabutine, rifapentine, rimexolone, ritanovir, rizatriptan, rosigiltazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terzosin, tetrahydrocannabinol, tiagabine, ticlopidine, tirofibran, tizanidine, topiramate, topotecan, toremifene, tramadol, tretinoin, troglitazone, trovafloxacin, valsartan, venlafaxine, vertoporfin, vigabatrin, vitamin A, vitamin D, vitamin E, vitamin K, zafirlukast, zileuton, zolmitriptan, zolpidem, zopiclone, and combinations thereof. Salts, isomers and/or other derivatives of the above-listed lipophilic bioactive agents may also be used, as well as combinations thereof.

In embodiments, coenzyme Q10 may be utilized as the lipophilic bioactive agent in accordance with the present disclosure. For example, coenzyme Q10 may be applied as described in International Publication No. WO 2005/069916, the entire disclosure of which is incorporated by reference herein. Coenzyme Q10, sometimes referred to herein as CoQ10, ubiquinone, or ubidecarenone, is a popular nutritional supplement and can be found in capsule form in nutritional stores, health food stores, pharmacies, and the like, as a vitamin-like supplement to help protect the immune system through the antioxidant properties of ubiquinol, the reduced form of CoQ10. CoQ10 is found throughout most tissues of the human body and the tissues of other mammals and is concentrated in the mitochondria. CoQ10 is very lipophilic and, for the most part, insoluble in water.

Other related compounds which may be administered instead of, or in combination with, CoQ10 include, but are not limited to, benzoquinones, isoprenoids, farnesols, farnesyl acetate, farnesyl pyrophosphate, 1-phenylalanine, d-phenylalanine, dl-phenylalanine, l-tyrosine, d-tyrosine, dl-tyrosine, 4-hydroxy-phenyl pyruvate, 4-hydroxy-phenyllactate, 4-hydroxy-cinnamate, dipeptides and tripeptides of tyrosine or phenylalanine, 3,4-dihydroxymandelate, 3-methoxy-4-hydroxyphenylglycol, 3-methoxy-4-hydroxymandelate, vanillic acid, phenylacetate, pyridoxine, S-adenosyl methionine, panthenol, mevalonic acid, isopentyl pyrophosphate, phenylbutyrate, 4-hydroxy-benzoate, decaprenyl pyrophosphate, beta-hydroxybutyrate, 3-hydroxy-3-methyl-glutarate, acetylcarnitine, acetoacetylcarnitine, acetylglycine, acetoacetylglycine, carnitine, acetic acid, pyruvic acid, 3-hydroxy-3-methylglutarylcarnitine, all isomeric forms of serine, alanine, cysteine, glycine, threonine, hydroxyproline, lysine, isoleucine, and leucine, even carbon number C4 to C18 fatty acids (butyric, caproic, caprylic, capric, lauric, myristic, palmitic, and stearic acids) salts of carnitine and glycine, e.g., palmitoylcarnitine and palmitoylglycine, and 4-hydroxy-benzoate polyprenyltransferase, any salts of these compounds, as well as any combinations thereof, and the like.

In embodiments, it may be desirable to form a stable, skin penetrating bioactive agent/liposomal concentrate for delivery of the lipophilic bioactive agent. Thus, in forming a liposome, it may be desirable to combine the lipophilic bioactive agent with a material that can solubilize the lipophilic bioactive agent in a suitable media, in some embodiments water, for subsequent encapsulation in a liposome. Suitable materials which may be utilized as a solubilizer for the lipophilic bioactive agent include, for example, polyoxyalkylene dextrans, fatty acid esters of saccharose, fatty alcohol ethers of oligoglucosides (e.g., alkylpolyglucosides, including those commercially available as TRITONT" from Dow Chemical North America, Midland, Mich., USA), fatty acid esters of glycerol (e.g., glycerol mono/distearate or glycerol monolaurate), and polyoxyethylene type compounds (e.g., polyoxyethylene, polyethylene glycol, polyethylene oxide, and copolymers thereof, including those commercially available as SOLUTOLT™ CREOMOPHOR™, MACROGOL™, CARBOWAX™, and POLYOXYL™).

Suitable solubilizers also include polyethoxylated fatty acid esters of sorbitan (e.g., polysorbates, including those commercially available as TWEEN™ and SPAN™) fatty acid esters of poly(ethylene oxide) (e.g., polyoxyethylene stearates), fatty alcohol ethers of poly(ethylene oxide) (e.g., polyoxyethylated lauryl ether), alkylphenol ethers of poly(ethylene oxide) (e.g., polyethoxylated octylphenol), polyoxyethylene-polyoxypropylene block copolymers (also known as poloxamers, including those commercially available as "PLURONICS"), and ethoxylated fats and oils (e.g., ethoxylated castor oil, or polyoxyethylated castor oil, also known as polyethylene glycol-glyceryl triricinoleate). Combinations of these solubilizers may also be utilized in embodiments. Such combinations are available from standard commercial sources.

In some embodiments, suitable solubilizers include polysorbates, e.g. those sold under the name TWEEN™. Examples of such polysorbates include polysorbate 80 (TWEEN™ 80), polysorbate 20 (TWEEN™ 20), polysorbate 60 (TWEEN™ 60), polysorbate 65 (TWEEN™ 65), polysorbate 85 (TWEEN™ 85), and the like, and combinations including these materials with other similar surfactants, including ARLACEL® surfactants commercially available from ICI Americas, as long as the HLB (Hydrophile-Lipophile Balance) of the surfactant and surfactant mixture favors the formation of an O/W type emulsion system.

To assist in solubilization, it may be desirable, in embodiments, to heat the lipophilic bioactive agent and solubilizer for a suitable period of time. The temperature of heating and time of heating may depend upon the specific lipophilic bioactive agent, the intrinsic thermal stability of the bioactive agent, and the specific solubilizer to be utilized. For example, in embodiments the lipophilic bioactive agent and solubilizer may be heated to a temperature from about 40° C. to about 65° C., in embodiments from about 50° C. to about 55° C., for a period of time from about 5 minutes to about 60 minutes, in embodiments from about 15 minutes to about 30 minutes. The heating time and solubilization of the lipophilic active agent may be reduced if the lipophilic active and solubilizer mixture is agitated. The weight ratio of lipophilic bioactive agent to solubilizer may be about 1:1, in embodiments from about 1:1 to about 4:2, in other embodiments from about 1:2 to about 3:2.

In embodiments, a solubilizer such as polysorbate 80 may be capable of dissolving lipophilic bioactive agent, in embodiments CoQ10, at high levels, with the lipophilic bioactive agent completely soluble in the solubilizer at a ratio of from about 1:2 to about 3:2, when heated to from about 50° C. to about 55° C., a temperature which exceeds the melting point of CoQ10 (which is from about 47° C. to about 48° C.).

The amount of solubilizer added to the lipophilic bioactive agent will depend upon the solubilizer, the lipophilic bioactive agent, and the phospholipids utilized to form the liposomes. In embodiments, a composition of the present disclosure possessing liposomes including a lipophilic bioactive agent therein may possess a solubilizer in an amount from about 0.2% to about 12% by weight, in embodiments from about 1.5% to about 6.5% by weight.

The solution of lipophilic bioactive agent and solubilizer, sometimes referred to herein as a first phase, may then be combined with the phospholipid as described above, in some embodiments lecithin. In embodiments, it may be desirable to place the phospholipid in a dispersion, sometimes referred to herein as a second phase, to which the solution of lipophilic bioactive agent and solubilizer (i.e., the first phase) are added. Suitable solvents for forming a dispersion/second phase including the phospholipid include, but are not limited to, water, purified water, deionized water, ethanol, isopropanol, glycols, diglycols, polyglycols, combinations thereof, and the like. Where added, the solvent may be present in an amount from about 70% by weight to about 98% by weight of the second dispersion, in embodiments from about 78% by weight to about 93% by weight of the second dispersion, with the phospholipid being present in an amount from about 2% by weight to about 30% by weight of the second dispersion, in embodiments from about 7% by weight to about 22% by weight of the second dispersion.

In embodiments, the phospholipid may be present in an amount of from about 1% by weight to about 20% by weight of the combination of phospholipid, solubilizer, and lipophilic bioactive agent, in embodiments from about 4% by weight to about 12% by weight of the combination of phospholipid, solubilizer, and lipophilic bioactive agent.

In embodiments, solubilization of a lipophilic bioactive agent such as CoQ10 in a material that has both lipophilic and hydrophilic properties, in embodiments a polysorbate such as polysorbate 80, may assist in liposome formulation by forming water-dispersible CoQ10 for encapsulation by a high phosphatidylcholine lecithin, such as PHOSPHOLIPON® 85G.

In some embodiments, additional components may be combined with this second phase to enhance formulation of the liposomes possessing a lipophilic bioactive agent, to improve overall rheological and processing properties, and to insure microbiological integrity of the resulting liposomal concentrate during storage. Such components include, without limitation, absorbents, antifoaming agents, acidifiers, alkalizers, buffers, antimicrobial agents, antioxidants (for example tocopherols, BHT, polyphenols, phytic acid) binders, biological additives, chelating agents (for example, disodium EDTA, tetrasodium EDTA, sodium metasilicate, and the like), denaturants, preservatives (for example imidazolidinyl urea, diazolidinyl urea, phenoxyethanol, methylparaben, ethylparaben, propylparaben, and the like), reducing agents, solubilizing agents, solvents, viscosity modifiers, humectants, thickening agents, and combinations thereof. These additional components may be present in an amount from about 0.001% by weight to about 10% by weight of the second phase, in embodiments from about 0.1% by weight to about 1% by weight of the second phase.

Examples of suitable humectants which may be added to the second phase include, but are not limited to, polyols and polyol derivatives, including glycerol, diglycerol, triglycerol, ethylene glycol, propylene glycol, butylene glycol, pentylene glycol (sometimes referred to herein as 1,2-pentane diol), isopreneglycol (1,4-pentane diol), 1,5-pentane diol, hexylene glycol, erythritol, 1,2,6-hexanetriol, polyethylene glycols such as PEG-4, PEG-6, PEG-7, PEG-8, PEG-9, PEG-10, PEG-12, PEG-14, PEG-16, PEG-18, PEG-20, combinations thereof, sugars and sugar derivatives (including fructose, glucose, maltose, maltitol, mannitol, inositol, sorbitol, sorbityl silanediol, sucrose, trehalose, xylose, xylitol, glucuronic acid and salts thereof), ethoxylated sorbitol (Sorbeth-6, Sorbeth-20, Sorbeth-30, Sorbeth-40), and combinations thereof. In some embodiments, a commercially available 1,2-pentane diol such as HYDROLITE-5® pentylene glycol (commercially available from Symrise GmbH) may be utilized. In other embodiments, a propylene glycol may be utilized. Where utilized, such humectants may be present in amounts from about 0.1% by weight to about 20% by weight of the second phase, in embodiments from about 3% by weight to about 10% by weight of the second phase.

In some embodiments, a preservative such as phenoxyethanol and a humectant such as butylene glycol, hexylene glycol, pentylene glycol and/or propylene glycol may both be added to the second phase. In embodiments, the pentylene glycold and/or propylene glycol may provide humectancy and assist in the preservation of the concentrate when combined with phenoxyethanol. The phenoxyethanol and pentylene glycol and/or propylene glycol mix should be water soluble and non-volatile. This is in contrast with the use of ethanol for preservation, which is often utilized by suppliers of liposomal dispersions. Where present, such preservatives may be present in amounts from about 0.01% by weight to about 3% by weight of the second phase, in embodiments from about 0.3% by weight to about 1% by weight of the second phase.

The dispersion containing the phospholipid, sometimes referred to herein as the second phase, and the solution containing the lipophilic bioactive agent and solubilizer, sometimes referred to herein as the first phase, may be homogenized by mixing at high shear to form a liposomal concentrate utilizing homogenizers, mixers, blenders and similar apparatus within the purview of those skilled in the art. In some embodiments, commercially available homogenizers including a Silverson L4RT Homogenizer or similar types of stator/rotor homogenizers made by Gifford-Wood, Frain, IKA and others, as well as multi-stage homogenizers, colloid mills, sonolators, or other types of homogenizers, may be used to produce submicron liposomal dispersions of the lipophilic bioactive agent. The stator/rotor type homogenizers described above have an operational range of from about 100 rpm to about 12,000 rpm, and may be supplied with a range of low shear, standard shear, and/or high shear head screens.

Homogenization may occur by mixing the two phases at suitable speeds of, for example, from about 4,000 rpm to about 12,000 rpm, in embodiments from about 5,000 rpm to about 10,000 rpm, in some embodiments about 7,000 rpm. The shear rate of the homogenizer may also be increased or decreased independent of the speed of the homogenizing shaft by increasing or decreasing the size of the processing screen surrounding the homogenizer head. In embodiments, liposomes may be made with both a standard emulsification screen and a high shear screen, for example, those screens supplied with the Silverson L4RT homogenizer. Mixing may occur for a suitable period of time of less than about 90 minutes, in embodiments from about 2 minutes to about 60 minutes, in embodiments from about 5 minutes to about 45 minutes. The resulting liposomes may have a particle size of less than about 600 nm, in embodiments from about 100 nm to about 500 nm, in other embodiments from about 200 nm to about 400 nm, in some embodiments about 300 nm.

In embodiments, the two phases may be separately heated to a temperature of from about 45° C. to about 65° C., in some embodiments from about 50° C. to about 55° C., and mixed with high shear homogenization at speeds and for periods of time described above to form submicron liposomes of CoQ10. Where the lipophilic bioactive agent is CoQ10, the processing temperature for the CoQ10 phase, the water/phospholipid phase, and the combined phases should not exceed about 55° C. in order to avoid oxidative degradation of the CoQ10. Processing the mixture at a temperature of from about 45° C. to about 55° C. may be useful to obtain a desired viscosity of the concentrate from about 5,000 cP to about 100,000 cP, in embodiments from about 15,000 cP to about 40,000 cP at a temperature of from about 35° C. to about 45° C. In some embodiments, processing for extended periods, e.g., for up to about 60 minutes at the speeds noted above within this temperature range, should not adversely impact the integrity of the resulting liposomes.

The bioactive agent may be present in the resulting concentrate in an amount of from about 10% by weight of the concentrate to about 30% by weight of the concentrate, in embodiments from about 18% by weight of the concentrate to about 26% by weight of the concentrate, in some embodiments from about 21% by weight of the concentrate to about 22% by weight of the concentrate. The amount of phospholipids in the concentrate may be from about 1% by weight of the concentrate to about 20% by weight of the concentrate, in embodiments from about 4% by weight of the concentrate to about 12% by weight of the concentrate, with the balance being the solubilizer, solvent, humectant and preservative.

In embodiments, it may be desirable to include a permeation enhancer in any composition including the liposomes described above. The permeation enhancer may increase the bioavailability of the resulting liposomes containing the lipophilic bioactive agent. While liposomes of the present disclosure may be administered by any route within the purview of those skilled in the art, the addition of a permeation enhancer may be especially beneficial for topical routes of administration.

Suitable permeation enhancers include, but are not limited to, ethoxydiglycol (also known as diethylene glycol monoethyl ether, commercially available as TRANSCUTOL and TRANSCUTOL P from Gattefosse and TRIVALIN CG from Tri-K Industries), 1,3-butylene glycol, isopentyl diol, 1,2-pentane diol, propylene glycol, 2-methyl propan-2-ol, propan-2-ol, ethyl-2-hydroxypropanoate, hexan-2,5-diol, di(2-hydroxypropyl)ether, pentan-2,4-diol, acetone, polyoxyethylene(2) methyl ether, 2-hydroxypropionic acid, 2-hydroxyoctanoic acid, propan-1-ol, 1,4 dioxane, tetrahydrofuran, butan-1,4-diol, propylene glycol dipelargonate, polyoxypropylene 15 stearyl ether, octyl alcohol, polyoxyethylene ester of oleyl alcohol, oleyl alcohol, lauryl alcohol, dioctyl adipate, dicapryl adipate, diisopropyl adipate, diisopropyl sebacate, dibutyl sebacate, diethyl sebacate, dimethyl sebacate, dioctyl sebacate, dibuyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, isopropyl palmitate, ethyl laurate, 2-ethyl-hexyl pelargonate, isopropyl isostearate, butyl laurate, benzyl benzoate, butyl benzoate, hexyl laurate, ethyl caprate, ethyl caprylate, butyl stearate, benzyl salicylate, 2-hyroxyoctanoic acid, dimethyl sulphoxide, methyl sulfonyl methane (MSM), n,n-dimethyl acetamide, n,n-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, 1-dodecylazacyloheptan-2-one, combinations thereof, and the like.

The amount of permeation enhancer in the compositions of the present disclosure, including any combination of any and all phases described herein, may be less than about 25% by weight of the composition, in embodiments from about 0.5% by weight to about 20% by weight of the composition, in other embodiments from about 3% by weight to about 15% by weight of the composition, in yet other embodiments from about 5% by weight of the composition to about 10% by weight of the composition.

In embodiments, a suitable permeation enhancer may include ethoxydiglycol. In other embodiments, a suitable permeation enhancer may include ethoxydiglycol in combination with another permeation enhancer such as propylene glycol, pentylene glycol, or any other permeation enhancer described above.

Surprisingly, and as detailed below in the Examples, it has been discovered that, in some embodiments, lower amounts of ethoxydiglycol, rather than higher amounts of ethoxydiglycol, optionally in combination with other permeation enhancers, may provide enhanced bioavailability of a lipophilic bioactive agent, in embodiments CoQ10, when administered topically. In embodiments, suitable amounts of ethoxydiglycol may be from about 0.5% to about 10% by weight of the composition, in embodiments from about 2% to about 8% by weight of the composition, in embodiments from about 4% to about 6% by weight of the composition.

Once formed, the resulting liposomes, which may be in a concentrate, may be administered to a patient or, in embodiments, may be combined with any pharmaceutically acceptable carrier. As used herein the terms "pharmaceutically acceptable carrier" and "pharmaceutically acceptable carriers" refers to those compounds which are, within the scope of sound medical judgment, suitable for use in contact with the tissues of a subject without undue toxicity, irritation, allergic response, and the like, commensurate with a reasonable benefit/risk ratio, and effective for their intended use, as well as salts and biocompatible derivatives of those compounds. As used herein, a pharmaceutically acceptable carrier includes any and all solvents, including water, dispersion media, coatings, antibacterial and antifungal agents, stabilizing excipients, absorption enhancing or delaying agents, polymers, including polymeric binders and polymeric adhesives, combinations thereof, and the like. Such materials should be non-toxic to the recipients at the dosages and concentrations employed, and may include buffers such as TRIS HCl, phosphate, citrate, acetate and other organic acid salts; antioxidants such as ascorbic acid; low molecular weight (less than about ten residues) peptides such as polyarginine, proteins such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS and/or polyethylene glycol.

The use of such media and agents for pharmaceutically active substances is within the purview of those skilled in the art. Supplementary active ingredients can also be incorporated into the compositions.

In embodiments, the above carriers may be utilized alone or in combination to form a carrier system. Suitable pharmaceutically acceptable carrier systems are within the purview of those skilled in the art and may include, but are not limited to, lotions, creams, gels, emulsions, dispersions, solids, solid sticks, semi-solids, aerosol or non-aerosol foams, sprays, serums, transdermal adhesive patch systems, combinations thereof, and the like. In embodiments, the liposomes may be in a liposomal concentrate and may be introduced to a patient with a permeation enhancer as described above. In embodiments, the permeation enhancer may be present in a water phase added to the liposomal concentrate to form a composition of the present disclosure. In embodiments, the formulation may be used for transdermal delivery.

Lotions or creams including the liposomes described above may include additional phases for formation of the lotion and/or cream. For example, in some embodiments, a composition of the present disclosure may include a lotion formed by combining the liposomes described above and permeation enhancer with additional oil phases, water phases, neutralizing phases, pigments, combinations thereof, and the like. In embodiments, these combined phases may form the pharmaceutically acceptable carrier described above.

As also noted above, in embodiments the permeation enhancer may be in one of the additional phases, for example, the water phase.

Similarly, the concentrate described above may be placed in any suitable solvent, including water, for administration, or combined with a polymeric binder and/or adhesive for administration as a solid, semi-solid, and the like. Emulsions and/or dispersions may be formed by combining the liposomal concentrate with surfactants utilizing any means within the purview of those skilled in the art.

Where additional phases are present in the formation of a composition of the present disclosure in the form of a lotion or cream, the liposome concentrate or dispersion may be present in an amount of from about 0.1% to about 30% by weight of the lotion or cream, in embodiments from about 5 to about 25% by weight of the lotion or cream.

The bioactive agent may thus be present in the final composition, in embodiments a lotion, cream or any other suitable form described above, in amounts of from about 0.5% by weight to about 20% by weight of the composition, in embodiments from about 0.75% by weight to about 10% by weight of the composition, in other embodiments from about 1% by weight to about 7.5% by weight of the composition, in other embodiments from about 1.25% by weight to about 5% by weight of the composition, in other embodiments from about 1.5% by weight to about 3% by weight of the composition.

For example, in some embodiments a lotion or cream including the liposome concentrate described above may include an oil phase which, in turn, may include emollients, fatty alcohols, emulsifiers, combinations thereof, and the like. For example, an oil phase could include emollients such as C12-15 alkyl benzoates (commercially available as FINSOLV™ TN from Finetex Inc. (Edison, N.J.)), capric-caprylic triglycerides (commercially available from Huls as MIGLYOL™ 812), and the like. Other suitable emollients which may be utilized include vegetable derived oils (corn oil, safflower oil, olive oil, macadamian nut oil, etc.); various synthetic esters, including caprates, linoleates, dilinoleates, isostearates, fumarates, sebacates, lactates, citrates, stearates, palmitates, and the like; synthetic medium chain triglycerides, silicone oils or polymers; fatty alcohols such as cetyl alcohol, stearyl alcohol, cetearyl alcohol, lauryl alcohol, combinations thereof, and the like; and emulsifiers including glyceryl stearate, PEG-100 stearate, Glyceryl Stearate, Glyceryl Stearate SE, neutralized or partially neutralized fatty acids, including stearic, palmitic, oleic, and the like; vegetable oil extracts containing fatty acids, Ceteareth-20, Ceteth-20, PEG-150 Stearate, PEG-8 Laurate, PEG-8 Oleate, PEG-8 Stearate, PEG-20 Stearate, PEG-40 Stearate, PEG-150 Distearate, PEG-8 Distearate, combinations thereof, and the like; or other non-polar cosmetic or pharmaceutically acceptable materials used for skin emolliency within the purview of those skilled in the art, combinations thereof, and the like.

The emollients, in embodiments C12-15 alkyl benzoates, may be included for emolliency and spreadability. Where present, the emollient may be present in an amount from about 0.2% by weight to about 15% by weight of the total composition, in embodiments from about 2% by weight to about 6% by weight of the total composition. Alcohols such as cetyl alcohol and stearyl alcohol may be added to impart body or texture to a cream. Where both cetyl alcohol stearyl alcohol are utilized, the ratio of cetyl alcohol to stearyl alcohol may be from about 2:1 to about 1:2, with the waxy alcohols making up from about 1 to about 6 weight percent of the total composition, in embodiments from about 2% by weight to about 4% by weight of the total composition.

As noted above, this oil phase may also include emulsifiers. Suitable eumulsifiers include, but are not limited to, stearates including glyceryl stearate, PEG-100 stearate, glyceryl stearate SE, glyceryl stearate citrate, combinations thereof, and the like. In embodiments, a combination of stearates may be utilized in the oil phase as an emulsifier. For example, a glyceryl stearate and PEG-100 stearate mixture (in embodiments, a mixture of glyceryl stearate and polyethylene glycol 100 stearate commercially available as ARLACEL® 165 from ICI Americas) may be used as an emulsifier to form an oil-in-water (o/w) emulsion. In such a combination, the PEG-100 stearate may act as the primary emulsifier and the glyceryl stearate may be a co-emulsifier. The emulsifier may be present in an amount from about 2% by weight to about 8% by weight of the total composition, in embodiments from about 3% by weight to about 5% by weight of the total composition.

The weight ratio of emulsifier to emollients as described above in this oil phase may be from about 10:1 to about 1:2, in some embodiments from about 2:1 to about 1:1.

Where present, an oil phase may be present in an amount of from about 5% to about 20% by weight of a lotion or cream, in embodiments from about 8% to about 15% by weight of a lotion or cream. Lotions or creams formed with the above liposomes may also include a water phase, which may, in embodiments, include the permeation enhancer described above as well as those items combined to form the second phase described above, including humectants and preservatives. Thus, in embodiments, the water phase utilized in formation of a lotion or cream possessing liposomes as described herein may include the second phase described above. In addition, in embodiments it may be desirable to add a viscosity modifier, sometimes referred to herein as a viscosity agent, to provide the lotion and/or cream with a desired viscosity.

Suitable viscosity agents which may be added to the water phase include water soluble polymers, including anionic polymers and nonionic polymers. Useful polymers include vinyl polymers such as cross linked acrylic acid polymers with the CTFA name CARBOMER, pullulan, mannan, scleroglucans, polyvinylpyrrolidone, polyvinyl alcohol, guar gum, hydroxypropyl guar gum, xanthan gum, acacia gum, arabia gum, tragacanth, galactan, carob gum, karaya gum, locust bean gum, carrageenin, pectin, amylopectin, agar, quince seed (*Cydonia oblonga* Mill), starch (rice, corn, potato, wheat), algae colloids (algae extract), microbiological polymers such as dextran, succinoglucan, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble materials such as bentonite, aluminum magnesium silicate, laponite, hectonite, and anhydrous silicic acid. Combinations of the foregoing may also be used in embodiments. In some embodiments, a CARBOMER such as CARBOMER 940 may be added as a viscosity agent to control the rheological properties of the cream formulas and add stability to the primary emulsion.

Where utilized, a viscosity agent may be present in an amount from about 0.1% to about 2% by weight of the composition, in embodiments from about 0.25% to about 0.6% of the composition.

Alternatively, the water phase may contain other soluble humectants such as glycols, polyols, lactate salts, amino acids, peptides, sugars, urea, sodium PCA, hyaluronic acid, or salts thereof, or any other suitable humectant or water soluble or water-dispersible moisturizer within the purview of those skilled in the art. The weight ratio of humectants to permeation enhancer to preservative to viscosity agent may be from about 20:10:1:1 to about 10:20:1:1, in some embodiments from about 15:10:2:1 to about 10:15:1:1.

Thus, as noted above, the water phase utilized to form a lotion and/or cream of the present disclosure may include water, humectants, preservatives, viscosity agents, and permeation enhancers. For example, in embodiments a suitable water phase may include a combination of glycerine, pentylene glycol and/or propylene glycol, ethoxydiglycol, phenoxyethanol, water, and CARBOMER 940. Such a water phase may contain glycerine for skin moisturization and humectancy; propylene glycol for humectancy and to aid in skin penetration and to improve the microbiological preservation profile; ethoxydiglycol to enhance CoQ10 skin penetration of the liposomes; phenoxyethanol for microbiological preservation; purified water as the phase solvent, and CARBOMER 940 to control the rheological properties of the cream formulas and to add stability to the primary emulsion.

In some embodiments, the viscosity agent may be added to the water phase as a dispersion in a humectant as described above, optionally in combination with water, optionally in combination with a preservative as described above. For example, in embodiments CARBOMER 940 may be added as a dispersion such as a 2% dispersion containing CARBOMER 940 dispersed in a mixture of water, propylene glycol, and phenoxyethanol. This CARBOMER 940 dispersion may be made separately in a batch manufacturing process. Where a viscosity agent such as CARBOMER 940 is added as a separate dispersion to the water phase, the weight ratio of viscosity agent to humectant to preservative to water may be from about 0.3:2:0.05:10 to about 0.5:1:0.2:10, in some embodiments from about 0.1: 0.5:0.05:9 to about 0.2:1:0.1:9.

Where present, a water phase may be present in an amount of from about 60% to about 80% by weight of a lotion or cream, in embodiments from about 63% to about 71% by weight of a lotion or cream.

In some embodiments, a third phase, which may be referred to herein as a neutralization phase or buffer phase, may also be added in the formation of a cream or lotion. The components of such a phase may include, but are not limited to, water, amines including triethanolamine, triisopropanolamine, 2-amino-2-methyl-1,3-propanediol, tris(hydroxymethyl)amine, 2-aminobutanol, sodium hydroxide, potassium hydroxide, salts such as sodium lactate, potassium lactate, sodium citrate, potassium citrate, sodium or potassium mono-, di, or tri-phosphate, sodium borate, potassium borate, acids such as lactic acid, citric acid, phosphoric acid, boric acid, combinations thereof, and the like. The water may act as a solvent and a diluent for the other ingredients in this phase. The amine such as triethanolamine may act as a neutralizer of an acid component in the water phase, such as the CARBOMER acrylic acid copolymer; additional salts such as a sodium lactate solution (60% w/w in water) and additional acids such as lactic acid may be added as a buffer system to adjust and maintain the final pH of the cream at from about 4.8 to about 6, in some embodiments from about 5 to about 5.5 (within the natural pH range of the skin). In embodiments, a pH of about 5 or higher may be useful, as the CARBOMER 940 acrylic copolymer of the water phase or similar material should be fully neutralized and develop its full viscosity potential.

In embodiments a suitable amount of amine such as triethanolamine may be added so that it is present in an amount from about 0.5% to about 2% by weight of the final composition, in embodiments from about 1% to about 1.5% by weight of the final composition. A suitable amount of salt such as sodium lactate may be added so that it is present in an amount from about 0.5% to about 3% by weight of the final composition, in embodiments from about 1% to about 1.5% by weight of the final composition. In embodiments, a suitable amount of acid such as lactic acid may be added so that it is present in an amount from about 0% to about 1% by weight of the final composition, in some embodiments about 0.25% to about 0.75% by weight of the final composition, in some embodiments about 0.5% by weight of the final composition. The neutralizer and/or buffer may be added so that it is present in an amount from about 0.01% to about 10 by weight of the final composition, in embodiments from about 2% to about 4% by weight of the final composition.

Where present, the neutralizing phase may be present in an amount of from about 0.1% to about 15% by weight of a lotion or cream, in embodiments from about 5% to about 8% by weight of a lotion or cream.

In embodiments, where the lipophilic bioactive agent is CoQ10, a cream without a pigment may have a yellow-orange color. Thus, it may be desirable to add a pigment to any lotion or cream to cosmetically mask the color imparted by the drug. Any pigment suitable for cosmetic or pharmaceutical formulations may be combined with the liposomes of the present disclosure. Such pigments include, but are not limited to, titanium dioxide, iron oxides, zinc oxide, combinations thereof, and the like. In embodiments, a water-dispersible grade of titanium dioxide powder may be used for lightening the color of the final cream. The yellow-orange color of the cream, imparted by CoQ10, may be substantially reduced and may be cosmetically improved by the addition of titanium dioxide in an amount of up to about 1% by weight of the lotion or cream, in embodiments from about 0.2% to about 2% by weight of the lotion or cream. In addition to the inorganic pigments, water-soluble or water dispersible FD&C or D&C dyes, and/or pearlescent opacifying agents based on glyceryl stearate, or mixtures of glyceryl stearate and other pearlescent agents suitable for use in topical pharmaceutical compositions, may be utilized.

In some embodiments, the amount of preservatives utilized in a composition of the present disclosure including a lipophilic bioactive agent in liposomes may be reduced by the inclusion of additional additives including those described above. For example, the amount of preservatives may be reduced in a composition of the present disclosure by the addition of multifunctional diols including, but not limited to, 1,2-pentane diol, 1,4-pentane diol, hexylene glycol, propylene glycol, 1,3-butylene glycol, glycerol, diglycerol, combinations thereof, and the like. In addition, the amount of preservatives may be reduced by lowering the water activity, $A_w$, of the composition by the addition of humectants described above and through the addition of soluble salts, e.g., sodium lactate and lactic acid which are present in the buffer and neutralization phase of the embodiments described above.

In embodiments, other soluble ingredients may also be added to compositions of the present disclosure to reduce the level of preservatives necessary. Such additional soluble ingredients include, but are not limited to, pH adjusting and buffering agents, tonicity adjusting agents, wetting agents and the like, for example, sodium acetate, sodium chloride, potassium chloride, calcium chloride, sorbitan monolaurate, triethanolamine oleate, and the like. Other buffers which may be added include sodium hydroxide, potassium hydroxide, ammonium hydroxide, monoethanolamine, diethanolamine, triethanolamine, diisopropanolamine, aminomethylpropanol, trimethamine, tetrahydroxypropyl ethylenediamine, citric acid, acetic acid, lactic acid, and salts of lactic acid including sodium lactate, potassium lactate, lithium lactate, calcium lactate, magnesium lactate, barium lactate, aluminum lactate, zinc lactate, sodium citrate, sodium acetate, silver lactate, copper lactate, iron lactate, manganese lactate, ammonium lactate, combinations thereof, and the like. These additives may be added to any phase described above utilized in forming a cream or lotion, including the oil phase, water phase, neutralizing phase, pigment, combinations thereof, and the like.

In embodiments the use of the liposome concentrate described above in forming the compositions of the present disclosure may permit tailoring the production of various compositions having the bioactive agent at varying concentrations. For example, in embodiments, the liposome concentrate may have the bioactive agent at a concentration of from about 10 to about 15 times greater than the amount of bioactive agent in a final composition for administration to a patient. For manufacturing, a large batch of concentrate may be produced, and then multiple portions of the concentrate may be utilized to produce multiple compositions having the bioactive agent at varying concentrations. This permits great flexibility in tailoring the concentration of a bioactive agent in a composition of the present disclosure.

For example, in embodiments, a submicron liposome concentrate may be utilized to create a dosage range of treatment creams possessing a lipophilic bioactive agent. In embodiments, the liposome concentrate may be a CoQ10-solubilized, fluidized or emulsified within a high linoleic acid-phosphatidylcholine multilamella liposome. There are a few reasons for creating a liposome concentrate of lipophilic drug actives. For example, the creation of a drug-liposome-concentrate in its nascent form, without the addition of a cream, lotion, or other vehicles, may permit direct measurement of the drug active, the liposome particle size, and particle size distribution without interference from other additives, typically present in the final product form. For example, cream and lotion emulsions formed by the homogenization of an oil phase, a water phase, and suitable emulsifiers and coemulsifiers, as described herein may include oil-in-water emulsion particles ranging from submicron size to a preponderance of particles above one micron. Once a liposome dispersion or liposome concentrate, as described, is added to the other components or phases of the final cream or lotion vehicle, measurement of the drug-liposome particle size and particle size distribution as distinguished from the particles of O/W emulsion or other additives (e.g., pigment) becomes impractical, if not impossible.

The preparation of a drug-liposome concentrate may also help maintain the intrinsic stability and initial particle size distribution of the drug-liposome. In the embodiments described for Coenzyme Q10 liposome concentrates, the concentrate can be stored at a controlled room temperature (59-86° F.) for several months until needed for manufacture. Once required for production, the liposome concentrate may be added after the formation of the emulsion vehicle and at a temperature that will not adversely affect the drug-liposome particles.

The preparation of the drug-liposome concentrate may also allow for assay of the drug and confirmation of stability of the drug in the liposome prior to incorporation of the liposome concentrate in the final vehicle. Moreover, the formulation of a drug-liposome concentrate at a single concentration allows this concentrate to be used to create a wide range of final dosage concentrations of the drug. In embodiments, the drug-liposome concentrate of Coenzyme Q10 may contain about 21% or about 22% Coenzyme Q10 and may be used to make final compositions, sometimes referred to herein as products, containing Coenzyme Q10 in amounts from about 0.5% up to about 20% by weight of the final composition, in embodiments from about 0.75% by weight to about 10% by weight of the final composition. This range may be widened substantially depending on the dose requirements of the lipophilic active. As noted in the Examples below, in some embodiments the bioactive, such as Coenzyme Q10, may be present in amounts of from about 1.25% by weight of the final composition to about 5% by weight of the final composition, in other embodiments from about 1.5% by weight to about 5% by weight of the composition.

The resulting creams, lotions, and the like may have a long shelf-life; i.e., they may remain stable during storage for at least about 2 years, in embodiments from about 2 to about 10 years.

Such lotions and creams may be packaged in any suitable packaging within the purview of those skilled in the art, including metal or glaminate tubes. The resulting creams have acceptable patient use characteristics for aesthetic considerations of product application, e.g., acceptable "rub-in", skin feel, product odor, product color, and product transfer.

Compositions of the present disclosure may be utilized to administer lipophilic bioactive agents for the treatment of any disease or condition which may benefit from the application of the lipophilic bioactive agent, including those disclosed in International Publication No. WO 2005/069916, the entire disclosure of which is incorporated by reference herein. While the instant disclosure has discussed topical/transdermal formulations in some detail, depending on the specific conditions being treated, the liposomes containing lipophilic bioactive agents described above may also be formulated and administered by other systemic and/or local routes. Suitable routes of administration include, but are not limited to, other topical routes of administration, oral, rectal, inhalation, vaginal, transmucosal, intestinal, parenteral including intramuscular, subcutaneous, intramedullary, intrathecal, direct intraventricular, intravenous, intraperitoneal, intranasal, intraocular, intratumoral, combinations thereof, and the like.

Where the compositions are administered by injection, the compositions may be administered in a single bolus, multiple injections, or by continuous infusion (for example, intravenously or by peritoneal dialysis). For parenteral administration, the compositions may be formulated in a sterilized pyrogen-free form. Compositions of the present disclosure can also be administered in vitro to a cell (for example, to induce apoptosis in a cancer cell in an in vitro culture) by simply adding the composition to the fluid in which the cell is contained.

In some embodiments, compositions of the present disclosure may be utilized in the treatment of cancer. As used herein, "cancer" refers to all types of cancer or neoplasm or malignant tumors found in mammals, including, but not limited to: leukemias, lymphomas, melanomas, carcinomas and sarcomas.

As used herein, the terms "cancer," "neoplasm," and "tumor," are used interchangeably and in either the singular or plural form, refer to cells that have undergone a malignant transformation that makes them pathological to the host organism.

Primary cancer cells (that is, cells obtained from near the site of malignant transformation) can be readily distinguished from non-cancerous cells by well established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells.

When referring to a type of cancer that normally manifests as a solid tumor, a "clinically detectable" tumor is one that is detectable on the basis of tumor mass, e.g., by procedures such as CAT scan, MR imaging, X-ray, ultrasound or palpation, and/or which is detectable because of the expression of one or more cancer-specific antigens in a sample obtainable from a patient.

Examples of cancers include cancer of the brain, breast, pancreas, cervix, colon, head and neck, kidney, lung, nonsmall cell lung, melanoma, mesothelioma, ovary, sarcoma, stomach, uterus and Medulloblastoma.

The term "sarcoma" generally refers to a tumor which is made up of a substance such as embryonic connective tissue and is generally composed of closely packed cells embedded in a fibrillar or homogeneous substance. Examples of sarcomas which can be treated with the compositions of the present disclosure include, but are not limited to, chondrosarcoma, fibrosarcoma, lymphosarcoma, melanosarcoma, myxosarcoma, osteosarcoma, adipose sarcoma, liposarcoma, alveolar soft part sarcoma, ameloblastic sarcoma, botryoid sarcoma, chloroma sarcoma, chorine carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, telangiectatic sarcoma, and the like.

The term "melanoma" is taken to mean a tumor arising from the melanocytic system of the skin and/or other organs. Melanomas which can be treated with the compositions of the present disclosure include, but are not limited to, for example, acrallentiginous melanoma, amelanotic melanoma, benign juvenile I melanoma, Cloudman's melanoma, S91 melanoma, Harding-Passey melanoma, juvenile melanoma, lentigo maligna melanoma, malignant melanoma, nodular melanoma, subungual melanoma, superficial spreading melanoma, and the like.

The term "carcinoma" refers to a malignant new growth made up of epithelial cells tending to infiltrate the surrounding tissues which give rise to metastases. Carcinomas which can be treated with the compositions of the present disclosure include, but are not limited to, for example, acinar carcinoma, acinous carcinoma, adenocystic carcinoma, adenoid cystic carcinoma, carcinoma adenomatosum, carcinoma of the adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma moue, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solenoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and the like.

Additional cancers which can be treated with the compositions of the present disclosure include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary cancer, bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, prostate cancer, and the like.

In addition, and as noted above, however, the compositions of the present disclosure may also be utilized to administer a lipophilic bioactive agent for the treatment of any disease or condition that may benefit from the application of a lipophilic bioactive agent.

The following Examples are being submitted to illustrate embodiments of the present disclosure. These Examples are intended to be illustrative only and are not intended to limit the scope of the present disclosure. Also, parts and percentages are by weight unless otherwise indicated.

EXAMPLES

Example 1

A concentrate was produced with CoQ10 as the lipophilic bioactive agent. About 10 kilograms (kg) of polysorbate 80 was placed in a vacuum kettle and heated to a temperature of from about 50° C. to about 55° C. About 8.8 kg of CoQ10 was combined with the PHOSPHOLIPON® 85G, a vacuum was applied with the temperature maintained at from about 50° C. to about 55° C., and the contents mixed for about 15 minutes. The resulting material may be referred to herein as the CoQ10 phase or the first phase. The CoQ10 was dissolved in the polysorbate 80 with the vacuum kettle sealed, vacuum on, and temperature of the mix of polysorbate/CoQ10 from about 50° C. to about 55° C.

In a separate kettle, about 15.8 kg of water was heated to a temperature of from about 50° C. to about 55° C., and about 0.2 kg of phenoxyethanol and about 2 kg of HYDROLITE-5® pentylene glycol were added and mixed until clear and uniform. About 8 kg of PHOSPHOLIPON® 85G was then added until dispersed. The resulting material may be referred to herein as the water phase or the second phase. The water phase achieved a uniform dispersion and hydration of the lecithin and was added to the CoQ10/Polysorbate liquid as described below at a temperature from about 50° C. to about 55° C.

A Silverson in-line production scale homogenizer, similar to the Silverson L4RT model used for laboratory scale batches, was utilized to combine the two phases described above, i.e., the CoQ10 phase and the water phase. Homogenization occurred using the Silverson standard emulsion head screen by mixing at full capacity (from about 7000 rpm to about 10,000 rpm) for a total of about 5 minutes through a closed recirculating loop and under vacuum (from about 18 mm to about 20 mm Hg) at temperatures of from about 50° C. to about 55° C. with sweep agitation until the solubilized CoQ10 was completely encapsulated and uniformly dispersed thereby creating a thick, uniform liposomal dispersion. The resulting CoQ10 concentrate possessed CoQ10 at a concentration of about 22% by weight. The PHOSPHOLIPON® 85G concentration was about 8% by weight of the total composition, that is, of the combination of the two phases described above.

In separate experiments, a one kg laboratory batch of the 22% CoQ10 concentrate described above was produced and samples were taken at 5 minute intervals during homogenization. The particle size of the liposomes at the various sampling times was determined utilizing laser diffraction equipment (Malvern 2000) following the manufacturer's directions. Details of the homogenization process and the particle sizes obtained during homogenization are set forth below in Table 1.

TABLE 1

| Process time (minutes) | Silverson L4RT Head Speed | Avg. particle diameter(nm) | Particle Intensity; % < 300 nm | Approx. peak temp. exposure (° C.) |
|---|---|---|---|---|
| 5 | 7000 | 108 | 84.9 | 55 |
| 10 | 7000 | 162 | 57.8 | 65 |
| 15 | 7000 | 112 | 85.4 | 55 |
| 20 | 7000 | 149 | 67.0 | 62 |
| 30 | 7000 | 120 | 83.0 | 55 |
| 45 | 7000 | 107 | 85.0 | 55 |

As can be seen from Table 1, the CoQ10 concentrate formula and process described above was capable of producing liposomes with an average diameter of 107 nm and a particle distribution that included 85% of all liposomes produced within a size of from about 59 nm to about 279 nm. A short process time (about 5 minutes) produced a liposome dispersion of CoQ10 just as efficiently as a long process time (about 45 minutes). As can also be seen from the above, optimal liposome particles were obtained where the CoQ10 was not exposed to temperatures above about 55° C.

Example 2

A cross linked acrylic acid polymer dispersion was prepared for use as a viscosity agent in a cream composition. The acrylic acid utilized, CARBOMER 940, was prepared in a 2% dispersion with the following components set forth below in Table 2:

TABLE 2

| Phase | Trade Name | CTFA Name | Percent | Amount (Kg) |
|---|---|---|---|---|
| 1 | phenoxyethanol | phenoxyethanol | 0.500 | 0.0750 |
| 1 | hydrolite-5 | pentylene glycol | 5.000 | 0.7500 |
| 2 | purified water, USP | water | 92.500 | 13.8750 |
| 3 | ACRITAMER 940 | CARBOMER 940 | 2.000 | 0.3000 |
|  | Totals |  | 100.000 | 15.0000 |

The manufacturing process was conducted as follows. The equipment was first cleaned and sanitized. On a benchtop, the phase 1 ingredients were mixed until clear and uniform. The required amount of water (phase 2) was weighed and added to a phase vessel kettle of the homgenizer described above in Example 1. The water was heated with a hot water/steam jacket to a temperature of from about 60° C. to about 65° C. Phase 1 was then added to the phase 2 water with moderate agitation until clear and uniform. The phase 1 container was rinsed with process water and the temperature was maintained at from about 60° C. to about 65° C. The agitator was then turned on high and CARBOMER 940 powder (phase 3) was added.

The temperature was maintained at from about 60° C. to about 65° C. and mixing continued at medium-high speed of from about 500 rpm to about 800 rpm until all the CARBOMER 940 powder was added. The CARBOMER powder was added slowly to the vortex of the mixture of phases 1 and 2. The powder was hand sifted slowly so that the total amount of CARBOMER was added in no less than about 10 minutes.

Mixing continued at medium-high agitation until all powder was thoroughly dispersed and no "fish-eyes" were present. The manufacturing process was conducted so that all of the unneutralized CARBOMER 940 powder was completely dispersed to create a smooth translucent dispersion of fully hydrated CARBOMER polymer. Agitation of the batch was high enough to create a visible vortex, but not so high to cause splashing of the batch. Adequate mixing of the batch occurred at a high speed of from about 800 rpm to about 1300 rpm over a period of time from about 60 minutes to about 90 minutes. The batch temperature was maintained at from about 60° C. to about 65° C. at the start of mixing and from about 55° C. to about 65° C. during mixing. The elevated temperature assisted in dispersion of the CARBOMER polymer and helped prevent agglomeration.

The batch was cooled to from about 25° C. to about 30° C. with chilled water through a jacket and mixing continued with medium-high agitation. Samples were taken to determine microquality, pH, specific gravity and viscosity.

Example 3

A cream emulsion base was formed utilizing several phases for combination with the CoQ10 concentrate possessing liposomes of Example 1. Phases A, B, C and D were combined to form the base cream. Phase E was the CoQ10 concentrate of Example 1 (22% w/w CoQ10). Details of the preparation of the cream emulsion base and the subsequent addition of the CoQ10 concentrate of Example 1 are set forth below.

For preparation of the cream possessing CoQ10 at 1.5% by weight, the procedure for combining the various phases was as follows with the ingredients set forth below in Tables 3-7:

TABLE 3

| CoQ10 Cream 1.5% | | | | |
|---|---|---|---|---|
| Phase | Trade Name | CTFA Name | Percent | Amount (g) |
| A | RITAMOLLIENT TN | C12-15 ALKYL BENZOATE | 5.000 | 1.0000 |
| A | RITA CA | CETYL ALCOHOL | 2.500 | 0.5000 |
| A | RITA SA | STEARYL ALCOHOL | 2.000 | 0.4000 |
| A | RITAPRO 165 | GLYCERYL | 4.500 | 0.9000 |

TABLE 3-continued

CoQ10 Cream 1.5%

| Phase | Trade Name | CTFA Name | Percent | Amount (g) |
|---|---|---|---|---|
| | | STEARATE AND PEG-100 STEARATE | | |

Phase A (the "Oil Phase") included C12-15 alkyl benzoates, which are light esters added for emolliency and spreadability. The cetyl alcohol and stearyl alcohol were waxes added to impart body or texture to the cream and the glyceryl stearate and PEG-100 stearate mixture was a primary emulsifier included to form an oil-in-water (o/w) emulsion. On a benchtop, the Phase A ingredients were weighed in a vacuum kettle and heated to from about 70° C. to about 75° C. in water bath.

TABLE 4

| Phase | Trade Name | CTFA Name | Percent | Amount (g) |
|---|---|---|---|---|
| B | RITA GLYCERIN | glycerin | 2.000 | 0.4000 |
| B | HYDROLITE-5 | pentylene glycol | 2.125 | 0.4250 |
| B | TRANSCUTOL P | ethoxydiglycol | 5.000 | 1.0000 |
| B | phenoxyethanol | phenoxyethanol | 0.463 | 0.0926 |
| B | ACRITAMER 940, 2% dispersion | water, CARBOMER 940 | 50.000 | 10.0000 |
| B | purified water USP | Water | 11.000 | 2.2000 |

Phase B (the "Water Phase"), contained glycerine for skin moisturization and humectancy; pentylene glycol for humectancy, to aid in skin penetration and to improve the microbiological preservation profile; ethoxydiglycol to enhance CoQ10 skin penetration of the liposomes; phenoxyethanol for microbiological preservation; purified water as the phase solvent, and CARBOMER 940 dispersion of Example 2 above to control the rheological properties of the cream formulas and to add stability to the primary emulsion.

Phase B ingredients were placed in a separate vacuum mixing kettle. The ingredients were mixed with moderate sweep mixing while heating to from about 70° C. to about 75° C. (no vacuum). When the Phase B ingredients reached from about 70° C. to about 75° C., Phase A ingredients were added at from about 70° C. to about 75° C. with moderate sweep mixing. The mixture of Phases A and B was recirculated through a Silverson homogenizer as described above in Example 1 (standard head) and continued to the next part of the process.

TABLE 5

| Phase | Trade Name | CTFA Name | Percent | Amount (g) |
|---|---|---|---|---|
| C | TEALAN 99% | triethanolamine | 1.300 | 0.2600 |
| C | RITALAC LA USP | lactic acid | 0.300 | 0.0600 |
| C | RITALAC NAL | Sodium lactate, water | 2.000 | 0.4000 |
| C | distilled water | Water | 3.312 | 0.6624 |

In Phase C (the "Neutralization and Buffer Phase"), purified water acted as a solvent and a diluent for the other ingredients in this phase. Triethanolamine was the primary neutralizer of the CARBOMER acrylic acid copolymer in the water phase (Phase B); sodium lactate solution (60% w/w in water) and lactic acid were added as a buffer system to adjust and maintain the final pH of the cream from about 5 to about 5.5, which is within the natural pH range of the skin.

On a benchtop, Phase C ingredients were weighed and mixed until uniform and heated to from about 60° C. to about 65° C. The Phase C mixture was then added to the vacuum mixing kettle containing Phases A and B with sweep mixer on medium-high.

Mixing continued while moving to the next part of the process.

TABLE 6

| Phase | Trade Name | CTFA Name | Percent | Amount (g) |
|---|---|---|---|---|
| D | TITANIUM DIOXIDE, #3328 | titanium dioxide | 1.000 | 0.2000 |

Phase D (the "Pigment Phase"). A water-dispersible grade of Titanium Dioxide powder was used in the formula solely for the purpose of lightening the color of the final cream color. The yellow-orange color of the cream, imparted by CoQ10, was substantially reduced and cosmetically improved by the addition of about 1% w/w Titanium Dioxide.

For Phase D of the process, weighed TiO2 was added to the batch (Phases A, B and C) and mixed and recirculated through the Silverson homogenizer (high shear head) for about 10 minutes or until completely uniform and fully extended (color was checked to confirm).

It was important to insure there was no agglomeration or clumping of the titanium dioxide on the sweep mixing blades; this was confirmed by visual inspection. A Silverson in line homogenizer as described above in Example 1 was used with a high shear screen to insure maximum deagglomeration and grinding of the titanium dioxide. The final dispersion of the titanium dioxide was checked with a Hegman PH-175 fineness of grind gauge.

TABLE 7

| Phase | Trade Name | CTFA Name | Percent | Amount (g) |
|---|---|---|---|---|
| E | CoQ10 CONCENTRATE 22% (From Example 1 above) | WATER, POLYSORBATE 80, UBIQUINONE, LECITHIN, PROPYLENE GLYCOL, PHENOXYETHANOL | 7.500 | 1.5000 |
| | Totals | | 100.000 | 20.000 |

Recirculation was stopped and the batch was cooled to from about 50° C. to about 55° C. with the sweep mixer on medium, at a speed of about 30 rpm. The previously weighed CoQ10 concentrate (Phase E) from Example 1 was warmed to from about 45° C. to about 50° C. and added to the batch (Phases A, B, C and D).

All phases were mixed with sweep agitation at about 60 rpm with a vacuum applied until uniform. Temperature was maintained at about 50° C.

The batch was cooled to from about 35° C. to about 45° C. with mixing at about 60 rpm and the application of a vacuum.

The resulting material was placed into holding containers.

For preparation of a cream possessing CoQ10 at 3% by weight, the exact same procedure described above for forming the cream possessing CoQ10 at 1.5% by weight was followed. The materials for each phase, and the amounts utilized, are set forth below in Tables 8-12:

TABLE 8

CoQ10 Cream 3%

| Phase | Trade Name | CTFA Name | Percent | Amount (g) |
|---|---|---|---|---|
| A | RITAMOLLIENT TN | C12-15 alkyl benzoate | 4.000 | 0.8000 |
| A | RITA CA | cetyl alcohol | 2.500 | 0.5000 |
| A | RITA SA | stearyl alcohol | 2.000 | 0.4000 |
| A | RITAPRO 165 | glyceryl stearate and PEG-100 stearate | 4.500 | 0.9000 |

TABLE 9

| Phase | Trade Name | CTFA Name | Percent | Amount (g) |
|---|---|---|---|---|
| B | RITA GLYCERIN | glycerin | 2.000 | 0.4000 |
| B | HYDROLITE-5 | pentylene glycol | 2.250 | 0.4500 |
| B | TRANSCUTOL P | ethoxydiglycol | 5.000 | 1.0000 |
| B | phenoxyethanol | phenoxyethanol | 0.463 | 0.0926 |
| B | ACRITAMER 940, 2% dispersion | water, CARBOMER 940 | 40.000 | 8.0000 |
| B | purified water, USP | water | 15.000 | 3.0000 |

TABLE 10

| Phase | Trade Name | CTFA Name | Percent | Amount (g) |
|---|---|---|---|---|
| C | TEALAN 99% | triethanolamine | 1.300 | 0.2600 |
| C | RITALAC LA | Lactic acid | 0.500 | 0.1000 |
| C | RITALAC NAL | sodium lactate, water | 2.000 | 0.4000 |
| C | purified water, USP | water | 2.487 | 0.4974 |

TABLE 11

| Phase | Trade Name | CTFA Name | Percent | Amount (g) |
|---|---|---|---|---|
| D | TITANIUM DIOXIDE, #3328 | titanium dioxide | 1.000 | 0.2000 |

TABLE 12

| Phase | Trade Name | CTFA Name | Percent | Amount (g) |
|---|---|---|---|---|
| E | CoQ10 CONCENTRATE 22% (From Example 1 above) | water, POLYSORBATE 80, ubiquinone, LECITHIN, pentylene glycol, phenoxyethanol | 15.000 | 3.0000 |
| | Totals | | 100.000 | 20.000 |

A similar cream was prepared by using the 22% CoQ10 concentrate from Example 1 in an amount of about 25% by weight to create a cream having COQ10 at a concentration of about 5% by weight.

A summary of the contents of CoQ10 creams having 1.5% CoQ10 by weight, 3% CoQ10 by weight, and 5% CoQ10 by weight are set forth below in Tables 13, 14 and 15 respectively. Note that in all the formulation examples given above and below for CoQ10 creams, the amount of concentrate used would actually yield a final theoretical concentration of about 10% above the target concentration. So, for "CoQ10 Cream, 1.5%", the actual batch amount used was 7.5% by weight of a 22% by weight concentrate that yielded 1.65% w/w CoQ10. The "CoQ10 Cream, 3%" was made with 15% by weight of the 22% by weight CoQ10 concentrate that yielded a theoretical content of 3.3% CoQ10 by weight. The 10% excess drug was added to extend the overall shelf life of the product and maintain the drug content from about 90% to about 110% of the label or expected drug content.

TABLE 13

CoQ10 CREAM, 1.5%

| Phase | Trade Name | INCI Name | Percent | Supplier |
|---|---|---|---|---|
| A | RITAMOLLIENT TN | C12-15 alkyl benzoates | 5.000 | RITA |
| A | RITA CA | cetyl alcohol | 2.000 | RITA |
| A | RITA SA | stearyl alcohol | 1.500 | RITA |
| A | RITAPRO 165 | glyceryl stearate and PEG-100 stearate | 4.500 | RITA |
| B | RITA GLYCERINE | Glycerine | 2.000 | RITA |
| B | HYDROLITE 5 | pentylene glycol | 2.125 | SYMRISE |
| B | TRANSCUTOL P | Ethoxydiglycol | 5.000 | GATTEFOSSE' |
| B | phenoxyethanol | Phenoxyethanol | 0.463 | RITA |
| B | PURIFIED WATER | deionized water | 11.000 | |
| B | ACRITAMER 940 dispersion, 2% | water, pentylene glycol, CARBOMER 940, phenoxyethanol | 50.000 | |
| C | purified water USP | water | 4.212 | |
| C | triethanolamine | triethanolamine | 1.300 | RITA |
| C | RITALAC NAL | sodium lactate and water | 2.000 | RITA |
| C | RITALAC LA USP | lactic acid | 0.400 | RITA |
| D | TITANIUM DIOXIDE #3328 | titanium dioxide | 1.000 | MPSI |

TABLE 13-continued

CoQ10 CREAM, 1.5%

| Phase | Trade Name | INCI Name | Percent | Supplier |
|---|---|---|---|---|
| E | CoQ10 liposome concentrate, 22% W/W (From Example 1) | water, POLYSORBATE 80, ubiquinone, lecithin, pentylene glycol, phenoxyethanol | 7.500 | |
| | Totals | | 100.000 | |

TABLE 14

CoQ10 Cream 3%

| Phase | Ingredient | % w/w |
|---|---|---|
| A | C12-C15 Alkyl Benzoate | 4.000 |
| A | Cetyl Alcohol | 2.000 |
| A | Stearyl Alcohol | 1.500 |
| A | Glyceryl Strearate & PEG 100 Stearate | 4.500 |
| B | Glycerin | 2.000 |
| B | Pentylene Glycol | 2.250 |
| B | Ethoxydiglycol | 5.000 |
| B | Phenoxyethanol | 0.476 |
| B | Carbomer | 40.000 |
| B | Purified Water | 16.000 |
| C | Sodium Lactate | 2.000 |
| C | Purified Water | 2.474 |
| C | Triethanolamine | 1.300 |
| C | Lactic Acid | 0.500 |
| D | Titanium Dioxide | 1.000 |
| E | CoQ10 Concentrate 22% (From Example 1) | 15.000 |
| | Total: | 100.000 |

TABLE 15

CoQ10 Cream 5%

| Phase | Ingredient | % w/w |
|---|---|---|
| A | C12-C15 Alkyl Benzoate | 3.000 |
| A | Cetyl Alcohol | 2.000 |
| A | Stearyl Alcohol | 1.500 |
| A | Glyceryl Strearate & PEG 100 Stearate | 4.500 |
| B | Glycerin | 2.000 |
| B | Pentylene Glycol | 2.000 |
| B | Ethoxydiglycol | 5.000 |
| B | Phenoxyethanol | 0.450 |
| B | Carbomer | 35.000 |
| B | Purified Water | 14.000 |
| C | Sodium Lactate | 2.000 |
| C | Purified Water | 0.750 |
| C | Triethanolamine | 1.300 |
| C | Lactic Acid | 0.500 |
| D | Titanium Dioxide | 1.000 |
| E | CoQ10 Concentrate 22% (From Example 1) | 25.000 |
| | Total: | 100.000 |

Note:
10% manufacturing overage of CoQ10 was added to the 1.5%, 3% and 5% batches (i.e., 1.5% plus 0.15%, 3% plus 0.3%, and 5% plus 0.5%).

Example 4

Creams possessing CoQ10 produced in Example 3 (i.e., 1.5%, 3%, and 5%) above were applied to porcine skin. The topical dose study was conducted on two pigs each, one male and one female. Each animal had 6 test areas; three test areas on each side. For each pig, one side (3 sites) was dosed once per day for 7 days, while the opposite test side (3 test areas) for each pig was dosed only one time on day 1. The creams from Example 3, prepared with ethoxydiglycol, were used on the male animals. The female animals received 3 test formulas that contained the same ingredients as the samples produced in Example 3 above, except they contained 5% 1,3-butylene glycol instead of 5% ethoxydiglycol. Details of these formulations made with 1,3-butylene glycol, which possessed 1.5% CoQ10 by weight, 3% CoQ10 by weight and 5% CoQ10 by weight, are set forth below in Tables 16, 17, and 18 respectively.

TABLE 16

CoQ10 Cream 1.5% Nominal Active Butylene Glycol Base

| Phase | Ingredient | % w/w |
|---|---|---|
| A | C12-C15 Alkyl Benzoate | 5.000 |
| A | Cetyl Alcohol | 2.000 |
| A | Stearyl Alcohol | 1.500 |
| A | Glyceryl Strearate & PEG 100 Stearate | 4.500 |
| B | Glycerin | 2.000 |
| B | Pentylene Glycol | 2.125 |
| B | Butylene Glycol | 5.000 |
| B | Phenoxyethanol | 0.463 |
| B | Carbomer | 50.000 |
| B | Purified Water | 11.001 |
| C | Sodium Lactate | 2.000 |
| C | Purified Water | 4.211 |
| C | Triethanolamine | 1.300 |
| C | Lactic Acid | 0.400 |
| D | Titanium Dioxide | 1.000 |
| E | CoQ10 Concentrate 22% (From Example 1) | 7.500 |
| | Total: | 100.000 |

TABLE 17

CoQ10 Cream 3% Nominal Active Butylene Glycol Base

| Phase | Ingredient | % w/w |
|---|---|---|
| A | C12-C15 Alkyl Benzoate | 4.000 |
| A | Cetyl Alcohol | 2.000 |
| A | Stearyl Alcohol | 1.500 |
| A | Glyceryl Strearate & PEG 100 Stearate | 4.500 |
| B | Glycerin | 2.000 |
| B | Pentylene Glycol | 2.250 |
| B | Butylene Glycol | 5.000 |
| B | Phenoxyethanol | 0.476 |
| B | Carbomer | 40.000 |
| B | Purified Water | 16.000 |
| C | Sodium Lactate | 2.000 |
| C | Purified Water | 2.474 |
| C | Triethanolamine | 1.300 |
| C | Lactic Acid | 0.500 |

TABLE 17-continued

CoQ10 Cream 3% Nominal Active Butylene Glycol Base

| Phase | Ingredient | % w/w |
|---|---|---|
| D | Titanium Dioxide | 1.000 |
| E | CoQ10 Concentrate 22% (From Example 1) | 15.000 |
| | Total: | 100.000 |

TABLE 18

CoQ10 Cream 5% Nominal Active Butylene Glycol Base

| Phase | Ingredient | % w/w |
|---|---|---|
| A | C12-C15 Alkyl Benzoate | 3.000 |
| A | Cetyl Alcohol | 2.000 |
| A | Stearyl Alcohol | 1.500 |
| A | Glyceryl Strearate & PEG 100 Stearate | 4.500 |
| B | Glycerin | 2.000 |
| B | Pentylene Glycol | 2.000 |
| B | Butylene Glycol | 5.000 |
| B | Phenoxyethanol | 0.450 |
| B | Carbomer | 35.000 |
| B | Purified Water | 14.000 |
| C | Sodium Lactate | 2.000 |
| C | Purified Water | 0.750 |
| C | Triethanolamine | 1.300 |
| C | Lactic Acid | 0.500 |
| D | Titanium Dioxide | 1.000 |
| E | CoQ10 Concentrate 22% (From Example 1) | 25.000 |
| | Total: | 100.000 |

All animals received the same dose of each formulation, which was 200 mg, to a 121 cm² application area applied once or daily for 7 days.

After application, skin samples were obtained and analyzed as follows. The skin test area was gently washed with a mild soap and water mixture (e.g., 1% Ivory Soap in water or equivalent) to remove any residual topical test formulation. If the area to be excised was larger than the dosed area, the dosed area was demarked with indelible ink to delineate the skin area that was dosed. A full thickness skin section was removed by scalpel with a size approximating 10 cm×10 cm, to the depth and including the adipose layer. Following excision, the skin section was laid flat and wrapped in two layers of plastic wrap (SARAN WRAP™ or equivalent), and frozen to about −70° C. or colder in a timely manner. Each skin section was identified as appropriate (e.g. animal identification, study number, date, etc.). Samples were maintained at about −70° C. or lower until examined.

Each skin section was placed in a water tight plastic bag and thawed in from about 30° C. to about 35° C. water baths. Once thawed, each skin section was gently rinsed with distilled deionized water to remove any residual surface dose and blood. All subcutaneous tissue (e.g. adipose) was removed by scalpel to the level of the papular dermis.

Each skin section was then tape stripped (TRANSPORE™, from 3M) from about 10 to about 20 times until approximately 10-25% surface glistening was observed. This process removed the stratum corneum and any residual surface dose.

On each full skin sheet, 6 areas were demarcated with ink. The demarcated areas were 1 cm² in area.

Each skin section was placed in a water tight plastic bag and immersed in a ~65° (±3°) C. water bath to initiate the separation process of the epidermis from the dermis. The test sites were then excised from the skin sheet by punch, and the epidermis removed from the dermis by forceps. The individual skin sections were weighed and the weight recorded. The individual skin sections were minced with a scalpel, placed into pre-labeled tubes, and saved for subsequent analysis.

The skin samples were extracted in isopropanol (IPA) on a shaker for about 47 hours, then stored at about −20° C. until further processed. The samples were then centrifuged at about 13,500 rpm for about 10 minutes and the supernatant was collected into 2 mL amber vials.

Quantification of CoQ10 was performed by High Performance Liquid Chromatography (HPLC-UV). Briefly, HPLC was conducted on a Hewlett-Packard 1100 Series HPLC system with an Agilent 1100 Series LC/MSD. A solvent system including about 65% Ethanol and about 35% Methanol was run through an Aquasil C18 column (about 3 mm×about 100 mm, 5μ) at a flow rate of about 1 mL/min. Ten microliters of sample were injected. Peak areas were quantified to concentration using an external standard curve prepared from the neat standard. The curve was spiked into IPA due to solubility issues of CoQ10 in water.

The results for the content of CoQ10 in mini-pig skin are summarized in FIGS. 1 and 2, and Tables 19 and 20 below. The 6 replicates per skin section were corrected to tissue weight and averaged to obtain a mean for each dosed site.

TABLE 19

Mean ± SD Tissue Weight (n = 42)

| Donor # | Epidermis (grams) | Dermis (gm) |
|---|---|---|
| 5061873 (Male) | 0.037 ± 0.012 | 0.682 ± 0.129 |
| 5061521 (Female) | 0.026 ± 0.007 | 0.603 ± 0.090 |

TABLE 20

Mean: ±SD Measured Concentration of CoQ10 in Porcine Skin (n = 6/section)

| Donor # | Sex | Side | Dose (mg) | Epidermis (μg/gm) | Dermis (μg/gm) |
|---|---|---|---|---|---|
| 5061873 | Male | Left | 1.5 | 137.7 ± 58.2 | 0.72 ± 1.12 |
| 5061873 | Male | Left | 3.0 | 188.7 ± 40.3 | <LLQ |
| 5061873 | Male | Left | 5.0 | 163.4 ± 39.1 | 0.16 ± 0.39 |
| 5061873 | Male | Right | 1.5 | 519.3 ± 101.2 | 0.93 ± 0.81 |
| 5061873 | Male | Right | 3.0 | 315.3 ± 227.0 | <LLQ |
| 5061873 | Male | Right | 5.0 | 331.2 ± 128.7 | <LLQ |
| 5061873 | Male | Center | 0 | 24.6 ± 11.5 | <LLQ |
| 5061521 | Female | Left | 1.5 | 135.6 ± 39.2 | <LLQ |
| 5061521 | Female | Left | 3.0 | 211.8 ± 60.5 | <LLQ |
| 5061521 | Female | Left | 5.0 | 211.9 ± 67.8 | <LLQ |
| 5061521 | Female | Right | 1.5 | 118.4 ± 32.6 | <LLQ |
| 5061521 | Female | Right | 3.0 | 84.7 ± 24.6 | <LLQ |
| 5061521 | Female | Right | 5.0 | 118.1 ± 26.6 | <LLQ |
| 5061521 | Female | Center | 0 | 25.7 ± 21.8 | <LLQ |

<LLQ = below lower level of quality validation range (i.e., not detected)

The data indicated that measurable amounts of CoQ10 were observed in all epidermal samples and in selected dermal samples.

All dosed sites for the epidermis were found to contain CoQ10 at levels that were significantly greater than the non-dosed sites (p<0.001).

There were no significant differences between the epidermal contents for CoQ10 across the three dosing concentrations in either the male or female pig skin sections (p>0.02)

Between the male and female pig, for the sites from the animal's right side (1-day dosing), the epidermal content for the 1.5% CoQ10 and 5% CoQ10 applied doses from the male's skin was significantly greater than that seen in the female's skin (p<0.003), but not for the 3% CoQ10 dose (p=0.0329). Thus, as can be seen from the data, the penetration of the CoQ10 on a single dose basis was significantly greater for the ethoxydiglycol formula vs. the butylene glycol formula (p<0.003 for the 1.5% and 5% doses and p=0.0329 for the 3% dose).

The epidermal levels for both male and female skin sections, for all three dose applications, for the 7-day dosing period (left side), were statistically identical.

Dermal content was only observed in the male skin sections for the 1.5% CoQ10 and 5% CoQ10 dose applications from the 7-day dosing period (left side), and the 1.5% CoQ10 dose application from the 1-day dosing period (right side).

A summary of the data is provided as follows in Table 21:

TABLE 21

| % Concentration | 1.5 | 3 | 5 |
| --- | --- | --- | --- |
| µg drug/mg formulation | 15 | 30 | 50 |
| Amount applied (mg): | 200 | 200 | 200 |
| Total drug applied (µg) | 3000 | 6000 | 10000 |
| Area applied (cm2) | 121 | 121 | 121 |
| µg Drug/cm$^2$ | 24.79 | 49.59 | 82.64 |
| Male Left side (×7 d) | | | |
| Epidermis (µg/cm$^2$) | 3.470 | 6.688 | 7.311 |
| % Dose/cm$^2$ | 14.0 | 13.5 | 8.8 |
| Dermis (µg/cm$^2$) | 0.575 | 0 | 0.106 |
| % Dose/cm$^2$ | 2.3 | 0.0 | 0.1 |
| Male Right side (×1 d) | | | |
| Epidermis (µg/cm$^2$) | 18.309 | 8.215 | 10.986 |
| % Dose/cm$^2$ | 73.8 | 16.6 | 13.3 |
| Dermis (µg/cm$^2$) | 0.582 | 0 | 0 |
| % Dose/cm$^2$ | 2.3 | 0.0 | 0.0 |

If one were to extrapolate the data from Table 21 to the total area of skin, the penetration of the CoQ10 would be as set forth below in Table 22.

TABLE 22

| | If expanded out to total area: | | |
| --- | --- | --- | --- |
| | 1.5 | 3 | 5 |
| Epidermis (µg/121 cm$^2$) | 419.87 | 809.248 | 884.631 |
| % Dose | 14.0 | 13.5 | 8.8 |
| Epidermis (µg/121 cm$^2$) | 2215.389 | 994.015 | 1329.306 |
| % Dose | 73.8 | 16.6 | 13.3 |

A single application of the CoQ10 cream formulation delivered an average of 12%, 17%, or 70% of the applied dose for the respective 5%, 3%, and 1.5% CoQ10 cream formulations. In general, the penetration of the CoQ10 on a single dose basis was significantly greater for the ethoxydiglycol formula vs. the butylene glycol formula (p<0.003 for the 1.5% and 5% doses and p=0.0329 for the 3% dose). The data indicated that there was a rise in epidermal content with applied concentration to 3% CoQ10 with the 5% CoQ10 dose being essential equal to the 3% CoQ10 dose. This suggests that the skin became saturated with CoQ10 at the 3% CoQ10 dose, or that the vehicle was unable to deliver more CoQ10 above the 3% CoQ10 concentration. It can be seen that the levels achieved in the skin following 7 days of topical application were identical between the 2 animals.

For the ethoxydiglycol formulations, and for the single application data, average penetration of 73.8%, 16.6%, and 13.3% for the respective 1.5%, 3% and 5% ethoxydiglycol containing creams was obtained.

An interesting and unexpected finding was the disproportional amount of CoQ10 found in the epidermis for the 1.5% cream, the lowest dose of CoQ10 tested. Without wishing to be bound by any theory, this enhanced penetration of CoQ10 may be a function of the ratio of CoQ10 to ethoxydiglycol in the cream formulations, or may possibly be related to the ratio of ethoxydiglycol to CoQ10 and the phospholipid liposome. The relatively higher ratio of ethoxydiglycol to CoQ10 used in the cream containing a lower concentration of CoQ10 may be responsible for the higher amounts of CoQ10 found in the epidermis.

The 1.5% cream and 3% cream also successfully completed 9 weeks accelerated testing (storage at about 35° C. and about 50° C.); passed 5 freeze-thaw cycles packaged in both plastic jar and metal tube packaging; and passed USP microbiological challenge testing. Results were confirmed for the same system with multiple development batches and at 1.5%, 3% and 5% by weight concentrations of CoQ10 in the cream prototype formulation base.

Example 5

Creams were produced as described in Example 3 above, except propylene glycol was utilized instead of pentylene glycol. A concentrate was first produced as described in Example 1 above, with the components listed below in Table 23:

TABLE 23

Batch Formula - CoQ 10 Concentrate

| | | Theoretical Quantity | |
| --- | --- | --- | --- |
| Phase | Raw Material Name | % w/w | kg |
| A | Polysorbate 80 NF | 25.000 | 5.000 |
| A | Ubidecarenone USP | 21.000 | 4.200 |
| B | Propylene Glycol USP | 10.000 | 2.000 |
| B | Phenoxyethanol NF | 0.500 | 0.100 |
| C | Purified Water USP | 35.500 | 7.100 |
| C | Lecithin NF | 8.000 | 1.600 |
| | Totals | 100.000 | 20.000 |

The resulting CoQ10 concentrate possessed CoQ10 at a concentration of about 21% by weight.

A CARBOMER dispersion was prepared as described in Example 2 above for use in forming the cream with the components listed below in Table 24:

TABLE 24

Batch Formula - Carbomer Dispersion

| | | Theoretical Quantity | |
| --- | --- | --- | --- |
| Phase | Raw Material Name | % w/w | Kg |
| A | Phenoxyethanol NF | 0.500 | 0.0900 |
| A | Propylene Glycol USP | 5.000 | 0.9000 |

TABLE 24-continued

Batch Formula - Carbomer Dispersion

| Phase | Raw Material Name | Theoretical Quantity | |
|---|---|---|---|
| | | % w/w | Kg |
| B | Purified Water USP | 92.500 | 16.6500 |
| C | Carbomer 940 NF | 2.000 | 0.3600 |
| | Totals | 100.000 | 18.000 |

A cream having 1.5% by weight CoQ10 and another cream having 3% by weight CoQ10 were prepared as described above in Example 3, with the components listed below in Tables 25 and 26:

TABLE 25

Batch Formula - CoQ1O Cream 1.5%

| Phase | Raw Material Name | Theoretical Quantity | |
|---|---|---|---|
| | | % w/w | kg |
| A | AlkylC12-15BenzoateNF | 5.000 | 1.000 |
| A | Cetyl Alcohol NF | 2.000 | 0.400 |
| A | Stearyl Alcohol NF | 1.500 | 0.300 |
| A | Glyceryl Stearate/PEG-100 Stearate | 4.500 | 0.900 |
| B | Glycerin USP | 2.000 | 0.400 |
| B | Propylene Glycol USP | 1.750 | 0.350 |
| B | Diethylene Glycol Monoethyl Ether NF | 5.000 | 1.000 |
| B | Phenoxyethanol NF | 0.463 | 0.093 |
| B | Carbomer Dispersion, 2% | 50.000 | 10.000 |
| B | Purified Water USP | 8.377 | 1.675 |
| B | Purified Water USP (for rinsing) | 3.000 | 0.600 |
| C | Trolamine NF | 1.300 | 0.260 |
| C | Lactic Acid USP | 0.400 | 0.080 |
| C | Sodium Lactate Solution USP, 60% | 2.000 | 0.400 |
| C | Purified Water USP | 4.210 | 0.842 |
| D | Titanium Dioxide USP | 1.000 | 0.200 |
| E | CoQ10 Concentrate, 21% | 7.500 | 1.500 |
| | Totals | 100.00 | 20.00 |

TABLE 26

Batch Formula - CoQ1O Cream 3%

| Phase | Raw Material Name | Theoretical Quantity | |
|---|---|---|---|
| | | % w/w | kg |
| A | AlkylC12-15BenzoateNF | 4.000 | 0.800 |
| A | Cetyl Alcohol NF | 2.000 | 0.400 |
| A | Stearyl Alcohol NF | 1.500 | 0.300 |
| A | Glyceryl Stearate/PEG-100 Stearate | 4.500 | 0.900 |
| B | Glycerin USP | 2.000 | 0.400 |
| B | Propylene Glycol USP | 1.500 | 0.300 |
| B | Diethylene Glycol Monoethyl Ether | 5.000 | 1.000 |
| B | Phenoxyethanol NF | 0.475 | 0.095 |
| B | Carbomer Dispersion, 2% | 40.000 | 8.000 |
| B | Purified Water USP | 13.725 | 2.745 |
| B | Purified Water USP (for rinsing) | 3.000 | 0.600 |
| C | Trolamine NF | 1.300 | 0.260 |
| C | Lactic Acid USP | 0.500 | 0.100 |
| C | Sodium Lactate Solution USP, 60% | 2.000 | 0.400 |
| C | Purified Water USP | 2.500 | 0.500 |
| D | Titanium Dioxide USP | 1.000 | 0.200 |
| E | CoQ10 Concentrate, 21% | 15.000 | 3.000 |
| | Totals | 100.000 | 20.000 |

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A composition comprising:
    a liposomal concentrate in combination with at least one pharmaceutically acceptable carrier possessing at least one permeation enhancer that comprises ethoxydiglycol;
    wherein the liposomal concentrate comprises:
        a phospholipid selected from the group consisting of lecithin, lysolecithin, phosphatidylcholine, phosphatidylethanolamine, phosphatidylinositol, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, and combinations thereof;
        Coenzyme Q10; and
        at least one solubilizer;
    wherein the composition comprises ethoxydiglycol in an amount from about 4% by weight to about 6% by weight of the composition and Coenzyme Q10 in an amount of from about 3% to about 3.3% by weight of the composition.

2. The composition of claim 1, wherein the composition is capable of providing a penetration of the Coenzyme Q10 to the epidermis of at least about 17%.

3. The composition of claim 1, wherein the composition comprises Coenzyme Q10 in an amount of about 3%.

4. The composition of claim 1, wherein the phospholipid is in combination with a solvent selected from the group consisting of water, purified water, deionized water, ethanol, isopropanol, glycols, diglycols, polyglycols, and combinations thereof.

5. The composition of claim 1, wherein the phospholipid is in combination with a formulation enhancer.

6. The composition of claim 5, wherein the formulation enhancer is an absorbent, antifoaming agent, acidifier, alkalizer, buffer, antimicrobial agent, antioxidant, binder, solubilizing agent, solvent, viscosity modifier, humectant, thickening agent, or combination thereof.

7. The composition of claim 1, wherein the Coenzyme Q10 is in combination with at least one additional bioactive agent.

8. The composition of claim 7, wherein the at least one additional bioactive agent is an acutretin, albendazole, albuterol, aminogluthemide, amiodarone, amlodipine, amphetamine, amphotericin B, atorvastatin, atovaquone, azithromycin, baclofen, beclomethsone, benezepril, benzonatate, betamethasone, bicalutanide, budesonide, bupropion, busulphan, butenafine, calcifediol, calciprotiene, calcitriol, camptothecan, candesartan, capsaicin, carbamezepine, carotenes, celecoxib, cerivistatin, cetrizine, chlorpheniramine, cholcalciferol, cilostazol, cimetidine, cinnarizine, ciprofloxacin, cisapride, clarithromycin, clemastine, clomiphene, clomipramine, clopidrogel, codeine, cyclobenzaprine, cyclosporine, danazol, dantrolene, dexchlopheniramine, diclofenac, dicoumarol, digoxin, dihydroepiandrosterone, dihydroergotamine, dihydrotachysterol, dirithromycin, donepezil, efavirenz, eposartan, ergocalciferol, ergotamine, essential fatty acid sources, etodolac, etoposide, famotidine, fenofibrate, fentanyl, fexofenadine, finasteride, flucanazole, flurbiprofen, fluvastatin, fosphenytion, frovatriptan, furazolidone, gabapentin, gemfibrozil, glibenclamide, glipizide, glyburide, glymepride, griseofulvin, halofantrine, ibuprofen, irbesartan, irinotecan, isosorbide dinitrate isotreinoin, itraconazole, ivermectin, ketoconazole, ketorolac, lamotrigine, lanosprazole, leflunomide, lisinopril, loperamide, loratadine, lovastatin, L-thryroxine, lutein, lycopene, medroxyprogesterone, mefepristone, mefloquine, megesterol acetate, methadone, methoxsalen, metronidazole, metronidazole, miconazole, midazolam, miglitol, minoxidil, mitoxantrone, montelukast, nabumetone, nalbuphine, naratiptan, nelfinavir, nifedipine, nilsolidipine, nilutanide, nitrofurantoin, nizatidine, omeprazole, oprevelkin, osteradiol, oxaprozin, paclitaxel, paricalcitol, paroxetine, pentazocine, pioglitazone, pizofetin, pravastatin, prednisolone, probucol, progesterone, pseudo-ephedrine, pyridostigmine, rabeprazole, raloxifene, refocoxib, repaglinide, rifabutine, rifapentine, rimexolone, ritanovir, rizatriptan, rosigiltazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terzosin, tetrahydrocannabinol, tiagabine, ticlidopine, tirofibran, tizanidine, topiramate, topotecan, toremifene, tramadol, tretinoin, troglitazone, trovafloxacin, valsartan, venlafaxine, vertoporfin, vigabatrin, vitamin A, vitamin D, vitamin E, vitamin K, zafirlukast, zileuton, zolmitriptan, zolpidem, zopiclone, or combination thereof.

9. The composition of claim 1, wherein the at least one pharmaceutically acceptable carrier is a solvent, buffer, antioxidant, antibacterial agent, antifungal agent, stabilizing excipient, absorption enhancing agent, absorption delaying agent, hydrophilic polymer, peptide, protein, monosaccharide, disaccharide, carbohydrate, chelating agent, sugar alcohol, surfactant, or combination thereof.

10. The composition of claim 1, wherein the ethoxydiglycol is in combination with at least one additional permeation enhancer.

11. The composition of claim 10, wherein the at least one additional permeation enhancer is a 1,3-butylene glycol, isopentyl diol, 1,2-pentane diol, propylene glycol, 2-methyl propan-2-ol, propan-2-ol, ethyl-2-hydroxypropanoate, hexan-2,5-diol, di(2-hydroxypropyl)ether, pentan-2,4-diol, acetone, polyoxyethylene(2)methyl ether, 2-hydroxypropionic acid, 2-hydroxyoctanoic acid, propan-1-ol, 1,4 dioxane, tetrahydrofuran, butan-1,4-diol, propylene glycol dipelargonate, polyoxypropylene 15 stearyl alcohol, poly-oxyethylene ester of oleyl alcohol, oleyl alcohol, lauryl alcohol, dioctyl adipate, dicapryl adipate, diisopropyl adipate, diisopropyl sebacate, dibutyl sebacate, diethyl sebacate, dimethyl sebacate, dioctyl sebacate, dibuyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, isopropyl palmitate, ethyl laurate, 2-ethyl-hexyl pelargonate, isopropyl isostearate, butyl laurate, benzyl benzoate, butyl benzoate, hexyl laurate, ethyl caprate, ethyl caprylate, butyl stearate, benzyl salicylate, 2-hyroxyoctanoic acid, dimethyl sulphoxide, methyl sufonyl methane, n,n-dimethyl acetamide, n,n-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar ester, tetrahydrofurfural alcohol, urea, diethyl-m-toluamide, 1-dodecylazacyloheptan-2-one, or combination thereof.

12. The composition of claim 1, wherein the at least one solubilizer is a polyoxyalkylene dextran, a fatty acid ester of saccharose, a fatty alcohol ether of oligoglucoside, a fatty acid ester of glycerol, a fatty acid ester of polyoxyethylene, a polyethoxylated fatty acid ester of sorbitan, a fatty acid ester of poly(ethylene oxide), a fatty alcohol ether of poly(ethylene oxide), a alkylphenol ether of poly(ethylene oxide), a polyoxyethylene-polyoxypropylene block copolymer, an ethoxylated oil, or a combination thereof.

13. The composition of claim 1, wherein the phospholipid comprises lecithin and the at least one permeation enhancer comprises propylene glycol in combination with the ethoxydiglycol.

14. The composition of claim 1, wherein the at least one pharmaceutically acceptable carrier includes an oil phase, an optional water phase, and an optional neutralization phase.

15. The composition of claim 14, wherein the at least one pharmaceutically acceptable carrier is selected from the group consisting of lotions and creams.

16. The composition of claim 14, wherein the oil phase comprises emollients, fatty alcohols, emulsifiers, or combinations thereof.

17. The composition of claim 16, wherein:
the emollient is a $C_{12-15}$ alkyl benzoate, capric-caprylic triglyceride, vegetable derived oil, caprate, linoleate, dilinoleate, isostearate fumarate, sebacate, lactate, citrate, stearate, palmitate, synthetic medium chain triglyceride, silicone oil, polymer or combination thereof;
the fatty alcohol is a cetyl alcohol, stearyl alcohol, cetearyl alcohol, lauryl alcohol or combination thereof; and
the emulsifier is a glyceryl stearate, polyethylene glycol 100 stearate, neutralized fatty acid, partially neutralized fatty acid, polyethylene glycol 150 stearate, polyethylene glycol 8 laurate, polyethylene glycol oleate, polyethylene glycol 8 stearate, polyethylene glycol 20 stearate, polyethylene glycol 40 stearate, polyethylene glycol 150 distearate, polyethylene glycol 8 distearate, or combination thereof.

18. The composition of claim 14, wherein the optional water phase comprises the at least one permeation enhancer in combination with a viscosity modifier.

19. The composition of claim 18, wherein the viscosity modifier is a cross linked acrylic acid polymer, pullulan, mannan, scleroglucans, polyvinylpyrrolidone, polyvinyl alcohol, guar gum, hydroxypropyl guar gum, xanthan gum, acacia gum, arabia gum, tragacanth, galactan, carob gum, karaya gum, locust bean gum, carrageenin, pectin, amylopectin, agar, quince seed, rice starch, corn starch, potato starch, wheat starch, algae extract, dextran, succinoglucan, carboxymethyl starch, methylhydroxypropyl starch, sodium alginate, alginic acid propylene glycol ester, sodium polyacrylate, polyethylacrylate, polyacrylamide, polyethyleneimine, bentonite, aluminum magnesium silicate, laponite, hectonite, anhydrous silicic acid, or combination thereof.

20. The composition of claim 14, wherein the optional water phase comprises water, glycerine, propylene glycol, ethoxydiglycol, phenoxyethanol, and cross linked acrylic acid polymers.

21. The composition of claim 14, wherein the optional neutralization phase comprises water, amines, sodium lactate, lactic acid, or a combination thereof.

22. The composition of claim 14, further comprising a pigment.

23. The composition of claim 22, wherein the pigment comprises titanium dioxide.

24. The composition of claim 14, wherein the oil phase comprises cetyl alcohol, stearyl alcohol, glyceryl stearate, polyethylene glycol stearate and one of $C_{12-15}$ alkyl benzoates and capric-caprylic triglyceride; the water phase comprises glycerine, propylene glycol, ethoxydiglycol, phenoxyethanol, purified water, and a cross linked acrylic acid polymer; and the neutralization phase comprises purified water, triethanolamine, sodium lactate, and lactic acid.

25. The composition of claim 1, wherein the at least one pharmaceutically acceptable carrier is a lotion or cream comprising:
- an oil phase comprising cetyl alcohol, stearyl alcohol, glyceryl stearate, and polyethylene glycol 100 stearate, and one of capric-caprylic triglyceride and $C_{12-15}$ alkyl benzoates, wherein the oil phase is present in an amount of from about 5% to about 20% by weight of the composition;
- a water phase comprising glycerin, propylene glycol, ethoxydiglycol, phenoxyethanol, water, and a cross-linked acrylic acid polymer, wherein the water phase is present in an amount of from about 60% to about 80% by weight of the composition;
- a neutralization phase comprising triethanolamine, sodium lactate, lactic acid, and water, wherein the neutralization phase is present in an amount of from about 0.1% to about 15% by weight of the composition; and
- a pigment comprising titanium dioxide in an amount of from about 0.2% by weight to about 2% by weight of the composition; and wherein the liposomal concentrate is present in the composition in an amount of from about 0.1% to about 30% by weight of the composition and wherein the liposomal concentrate comprises a polyethoxylated fatty acid ester of sorbitan, a phosphatidylcholine lecithin, phenoxyethanol, propylene glycol, and water.

26. The composition of claim 25, wherein the composition is capable of providing a penetration of the Coenzyme Q10 to the epidermis of at least about 17%.

27. The composition of claim 25, wherein the Coenzyme Q10 is present in an amount of about 3%.

28. The composition of claim 1, wherein the phospholipid is present in the composition in an amount of from about 0.15% by weight to about 5% by weight of the composition.

\* \* \* \* \*